United States Patent [19]
Bell et al.

[11] Patent Number: 5,965,553
[45] Date of Patent: *Oct. 12, 1999

[54] SQUALENE SYNTHETASE INHIBITORS

[75] Inventors: Andrew S. Bell, Sandwich, United Kingdom; Ernest S. Hamanaka, Gales Ferry, Conn.; Cheryl M. Hayward, Groton, Conn.; Douglas A. Scully, Noank, Conn.; Blanda Stammen, Sandwich, United Kingdom

[73] Assignee: Pfizer Inc., New York, N.Y.

[ * ] Notice: This patent is subject to a terminal disclaimer.

[21] Appl. No.: 08/874,089

[22] Filed: Jun. 12, 1997

Related U.S. Application Data
[60] Provisional application No. 60/019,894, Jun. 20, 1996.
[51] Int. Cl.$^6$ .................. A61K 31/55; C07D 267/08; C07D 281/08
[52] U.S. Cl. .................. 514/211; 540/488; 540/490; 540/547; 540/548; 540/552
[58] Field of Search .................. 514/211; 540/490, 540/552, 547, 548, 488

[56] References Cited

U.S. PATENT DOCUMENTS

| | | | |
|---|---|---|---|
| 5,488,149 | 1/1996 | Nomoto et al. | 562/449 |
| 5,698,691 | 12/1997 | Yukimasa et al. | 540/490 |
| 5,726,306 | 3/1998 | Yukimasa et al. | 540/490 |
| 5,753,649 | 5/1998 | Tahara et al. | 514/220 |
| 5,770,438 | 6/1998 | Nakahama et al. | 435/280 |
| 5,770,594 | 6/1998 | Hamanaka et al. | 514/211 |

FOREIGN PATENT DOCUMENTS

| | | |
|---|---|---|
| WO 96/09827 | 4/1996 | WIPO . |
| WO9620184 | 7/1996 | WIPO . |
| WO9710224 | 3/1997 | WIPO . |

OTHER PUBLICATIONS

Squalene Synthetase inhibitors, *Current Opinion in Therapetic Patents*, 1993, pp. 861–864.

*Primary Examiner*—Mukund J. Shah
*Assistant Examiner*—Brenda Coleman
*Attorney, Agent, or Firm*—Peter C. Richardson; Gregg C. Benson; A. Dean Olson

[57] ABSTRACT

This invention relates to certain benzoxazepinones and benzothiazepinones useful as hypocholesterolemic agents, hypotriglyceridemic agents, antiatherosclerosis agents, antifungal agents, Alzheimer's agents or anti-acne agents.

26 Claims, No Drawings

SQUALENE SYNTHETASE INHIBITORS

This application claims the benefit of U.S. Provisional Application No. 60/019,894 filed Jun. 20, 1996.

BACKGROUND OF THE INVENTION

This invention relates to squalene synthetase inhibitors, pharmaceutical compositions containing such inhibitors and the use of such inhibitors to treat hypercholesterolemia, hypertriglyceridemia, atherosclerosis, fungal infections, acne and Alzheimer's disease in mammals, including humans.

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including hydroxymethylglutaryl-coenzyme A (HMG-CoA) reductase, HMG-CoA synthase, squalene synthetase, squalene epoxidase, squalene cyclase and lanosterol demethylase. Inhibition of catalysis of these enzymes or blocking HMG-CoA reductase gene expression is recognized as an effective means to reduce cholesterol biosynthesis (thus inhibitors thereof are referred to as cholesterol synthesis inhibitors) and can lead to a reduction in cholesterol levels. For example, there are known HMG-CoA reductase inhibitors (e.g., lovastatin, simvastatin, pravastatin, fluvastatin, atorvastatin, rivastatin) that are used for the treatment of hypercholesterolemia.

Recently adopted National Cholesterol Education Program guidelines recommend aggressive lipid-lowering therapy for patients with pre-existing cardiovascular disease or for those with multiple factors that place them at increased risk.

The term squalene synthetase inhibitor refers to compounds that inhibit the condensation of 2 molecules of farnesylpyrophosphate to form squalene, a reaction that is catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A summary of squalene synthetase inhibitors has been compiled (Curr. Op. Ther. Patents (1993) 8614). European patent publication 0 567 026 A1 discloses certain 4,1-benzoxazepine derivatives as squalene synthase inhibitors and their use in the treatment of hypercholesterolemia and as fungicides. European patent publication 0 645 378 A1 discloses certain condensed seven- or eight-membered heterocycles as squalene synthetase inhibitors and their use in treatment and prevention of hypercholesterolemia and fungal infections. European patent publication 0 645 377 A1 discloses certain benzoxazepine derivatives as squalene synthetase inhibitors useful for the treatment of hypercholesterolemia or coronary sclerosis. European patent publication 0 611 749 A1 discloses certain substituted amic acid derivatives useful for treatment of arteriosclerosis. European patent publication 0705607 A2 discloses certain condensed seven- or eight-membered heterocyclic compounds useful as antihypertriglyceridemic agents. PCT Publication WO 96/09827 discloses certain combinations of cholesterol absorption inhibitors and cholesterol synthesis inhibitors including benzoxazepine derivatives and benzothiazepine derivatives. European patent publication 0710725 A1 discloses a process for producing certain optically active compounds, including benzoxazepine compounds, having plasma cholesterol and triglyceride lowering activities.

Thus, although there are a variety of hypercholesterolemia therapies, there is a continuing need and a continuing search in this field of art for alternative therapies.

SUMMARY OF THE INVENTION

This invention is directed to cholesterol synthesis inhibitor compounds of FORMULA I useful for the treatment of hypercholesterolemia, hypertriglyceridemia, atherosclerosis, fungal infections, Alzheimer's disease and acne.

The compounds of this invention have the Formula I

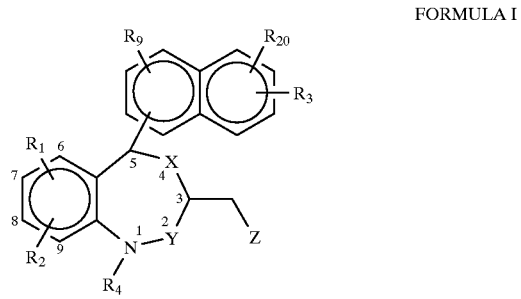

FORMULA I or the pharmaceutically acceptable cationic and anionic salts, prodrugs and stereoisomers thereof wherein X is oxy, thio, —S(O)— or —S(O)$_2$—;

Y is carbonyl or methylene;

$R_1$, $R_2$, $R_3$, $R_{20}$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$)alkoxy, fluorinated ($C_1$–$C_4$)alkoxy having from 1 to 9 fluorines, ($C_1$–$C_4$)alkylthio, ($C_1$–$C_4$) alkylsulfinyl, ($C_1$–$C_4$)alkylsulfonyl, phenyl, amino, mono-N- or di-N,N-($C_1$–$C_4$)alkylamino, carboxyl, ($C_1$–$C_4$)alkoxycarbonyl, carbamoyl, mono-N- or di-N, N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–C6) alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkenyl or $R_4$ is ($C_1$–$C_7$)alkyl, ($C_1$–$C_7$) alkenyl or ($C_3$–$C_4$)cycloalkylmethyl wherein said $(C_1-C_7)$alkyl, $(C_1-C_7)$alkenyl or $(C_3-C_4)$ cycloalkylmethyl are mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$ alkylsulfinyl, $(C_1-C_4)$alkylsulfonyl, mono-N- or di-N, N-$(C_1-C_4)$alkylamino, mono-N- or di-N,N-$(C_1-C_4)$ alkylaminocarbonyl, or mono-N-or di-N,N$(C_1-C_4)$ alkylaminosulfonyl; or $R_4$ is $(C_1-C_7)$alkyl substituted with 1 to 15 fluorines or $(C_3-C_4)$cycloalkylmethyl substituted with 1 to 9 fluorines; or $R_4$ is het$(C_1-C_6)$alkyl wherein het is a 4-7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, mono-N- or di-N, N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ $(C_1-C_4)$alkyl, N(R$_{12}$)COR$_{15}$

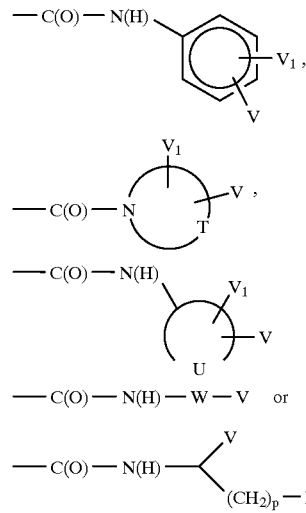

$R_{12}$, $R_{13}$ and $R_{14}$ are each independently H or $(C_1-C_4)$ alkyl;

$R_{15}$ is $(C_1-C_4)$alkyl;

$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$ alkylamino, carboxyl, $(C_1-C_4)$alkoxycarbonyl, carbamoyl or mono-N- or di-N,N-$(C_1-C_4)$ alkylcarbamoyl; phenyl optionally mono- or di-substituted independently with methyl, methoxyl, fluoro, trifluoromethoxyl, carboxyl, $(C_1-C_4)$ alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO$_2$R$_7$, hydroxyl or $(C_1-C_4)$alkoxy;

$R_7$ is hydrogen or $(C_1-C_4)$alkyl;

p is 1, 2, 3 or 4;

$R_5$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$ alkylsulfinyl, mono-N- or di-N,N-$(C_1-C_4)$ alkylcarbamoyl, mono-N- or di-N,N-$(C_1-C_4)$ alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$ alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

A preferred group of compounds, designated the "A Group", contains those compounds having the Formula I as shown above wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is oxy;

Y is carbonyl;

V is —CO$_2$R$_7$;

$V_1$ is H; and

Z is carboxyl, tetrazol-5-yl,

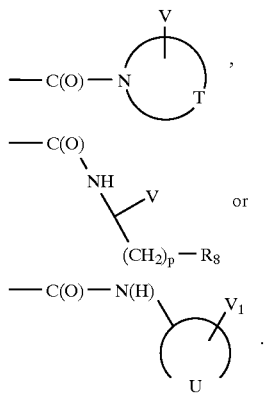

A group of compounds, which is preferred among the "A Group" of compounds designated the "B Group", contains those compounds wherein the $C^5$ substituent is 1-naphthyl;

T forms a piperidin-1-yl ring; and $R_8$ is carboxyl or alkylthio.

A group of compounds, which is preferred among the "B Group" of compounds designated the "C Group", contains those compounds wherein $R_4$ is 2,2-dimethyl-3-hydroxypropyl;
$R_1$ is 7-chloro;
$R_2$ is H; and
Z is carboxyl A group of compounds, which is preferred among the "B Group" of compounds designated the "D Group", contains those compounds wherein
$R_4$ is 2,2-di-(hydroxymethyl)propyl;
$R_1$ is 7-chloro;
$R_2$ is H; and
Z is carboxyl.

A group of compounds, which is preferred among the "B Group" of compounds designated the "E Group", contains those compounds wherein
$R_4$ is 3-carboxy-2,2-dimethylpropyl;
$R_1$ is 7-chloro;
$R_2$ is H; and
Z is carboxyl.

A preferred group of compounds, designated the "F Group", contains those compounds having the Formula I as shown above wherein
the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;
$R_3$, $R_{20}$ and $R_9$ are H;
X is oxy;
Y is methylene;
V is —$CO_2R_7$;
$V_1$ is H; and
Z is carboxyl, tetrazol-5-yl,

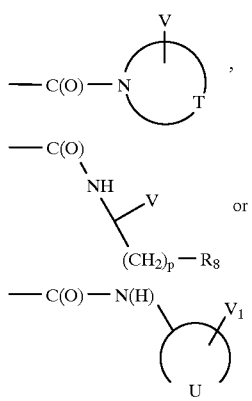

A group of compounds, which is preferred among the "F Group" of compounds designated the "G Group", contains those compounds wherein
the $C^5$ substituent is 1-naphthyl;

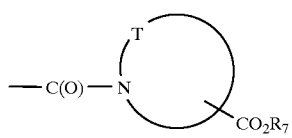

and T forms a piperidin-1-yl ring.

A preferred group of compounds, designated the "H Group", contains those compounds having the Formula I as shown above wherein the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;
$R_3$, $R_{20}$ and $R_9$ are H;
X is thio;
Y is carbonyl;
V is —$CO_2R_7$ or tetrazol-5-yl;
$V_1$ is H; and
Z is carboxyl, tetrazol-5-yl,

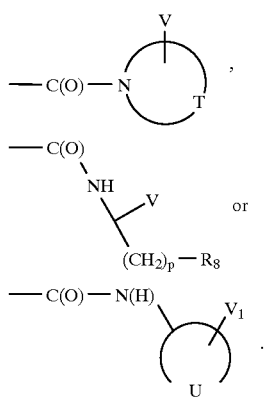

A group of compounds, which is preferred among the "H Group" of compounds designated the "I Group", contains those compounds wherein
the $C^5$ substituent is 1-naphthyl; and
T forms a piperidin-1-yl ring.

A group of compounds, which is preferred among the "I Group" of compounds designated the "J Group", contains those compounds wherein
$R_4$ is 2,2-dimethyl-3-hydroxypropyl;
$R_1$ is 7-chloro;
$R_2$ is H; and
Z is 4-carboxylpiperidin-1-yl-carbonyl.

An especially preferred compound within the "J Group" of compounds is the compound wherein the $C^3$ and $C^5$ carbons are each of the (R) configuration.

A preferred group of compounds, designated the "K Group", contains those compounds having the Formula I as shown above wherein
the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;
$R_3$, $R_{20}$ and $R_9$ are each independently halo, $(C_1-C_4)$ alkyl, $(C_1-C_4)$alkoxy, hydroxy, trifluoromethyl, $(C_1-C_4)$ alkylthio, fluorinated $(C_1-C_4)$alkoxy having from 1 to 9 fluorines, $(C_1-C_4)$alkanoyl, phenyl, amino, mono-N- or di-N,N-$(C_1-C_4)$alkylamino, carboxyl, $(C_1-C_4)$ alkoxycarbonyl;
X is oxy or thio;
Y is carbonyl or methylene;
V is —$CO_2R_7$ or tetrazol-5-yl;

$V_1$ is H; and

Z is carboxyl, tetrazol-5-yl,

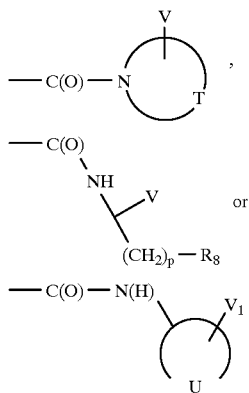

A preferred group of compounds, designated the "L Group", contains those compounds having the Formula I as shown above wherein Z is

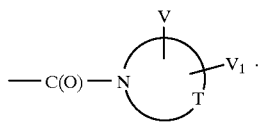

A group of compounds, which is preferred among the "L Group" of compounds designated the "M Group", contains those compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is oxy; and

Y is carbonyl.

A group of compounds, which is preferred among the "M Group" of compounds designated the "N Group", contains those compounds wherein the $C^5$ substituent is 1-naphthyl; and T forms a piperidin-1-yl ring.

A group of compounds, which is preferred among the "L Group" of compounds designated the "O Group", contains those compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_0-C_4)$ alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is oxy; and

Y is methylene.

A group of compounds, which is preferred among the "O Group" of compounds designated the "P Group", contains those compounds wherein the $C_5$ substituent is 1-naphthyl; and T forms a piperidin-1-yl ring.

A group of compounds, which is preferred among the "L Group " of compounds designated the "Q Group", contains those compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is thio; and

Y is carbonyl.

A group of compounds, which is preferred among the "Q Group" of compounds designated the "R Group", contains those compounds wherein the $C_5$ substituent is 1-naphthyl; and T forms a piperidin-1-yl ring.

A group of compounds, which is preferred among the "L Group" of compounds designated the "S Group", contains those compounds wherein the $C^3$ and $C_5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_{20}$ and $R_9$ are each independently halo, $(C_1-C_4)$ alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl, phenyl, amino, mono-N- or di-N,N-$(C_1-C_4)$alkylamino, carboxyl, $(C_1-C_4)$alkoxycarbonyl;

X is oxy or thio; and

Y is carbonyl or methylene.

Yet another aspect of this invention is directed to methods for treating hypercholesterolemia, hypertriglyceridemia, atherosclerosis, fungal infections, Alzheimer's disease and acne in a mammal (including a human being) by administering to a mammal suffering from hypercholesterolemia, hypertriglyceridemia, atherosclerosis, a fungal infection, Alzheimer's disease or acne a hypercholesterolemia, hypertriglyceridemia, atherosclerosis, anti-fungal, Alzheimer's disease or acne treating amount of a Formula I compound or the pharmaceutically acceptable cationic and anionic salts, prodrugs and stereoisomers thereof.

Yet another aspect of this invention is directed to a method for treating hypercholesterolemia in a mammal (including a human being) by administering to a mammal suffering from hypercholesterolemia a hypercholesterolemia treating amount of a Formula I compound or the pharmaceutically acceptable cationic and anionic salts, prodrugs and stereoisomers thereof.

Yet another aspect of this invention is directed to a method for treating hypertriglyceridemia in a mammal (including a human being) by administering to a mammal suffering from hypertriglyceridemia a hypertriglyceridemia treating amount of a Formula I compound or the pharmaceutically acceptable cationic and anionic salts, prodrugs and stereoisomers thereof.

Yet another aspect of this invention is directed to a method for treating atherosclerosis in a mammal (including a human being) by administering to a mammal suffering from atherosclerosis an atherosclerotic treating amount of a Formula I compound or the pharmaceutically acceptable cationic and anionic salts, prodrugs and stereoisomers thereof.

Yet another aspect of this invention is directed to a method for treating a fungal infection in a mammal (including a human being) by administering to a mammal suffering from a fungal infection an antifungal treating amount of a Formula I compound or the pharmaceutically acceptable cationic and anionic salts, prodrugs and stereoisomers thereof.

Yet another aspect of this invention is directed to a method for treating Alzheimer's disease in a mammal (including a human being) by administering to a mammal suffering from Alzheimer's disease an Alzheimer's disease treating amount of a Formula I compound or the pharmaceutically acceptable cationic and anionic salts, prodrugs and stereoisomers thereof.

Yet another aspect of this invention is directed to a method for treating acne in a mammal (including a human being) by administering to a mammal suffering from acne an acne treating amount of a Formula I compound or the pharmaceutically acceptable cationic and anionic salts, prodrugs and stereoisomers thereof.

This invention is also directed to pharmaceutical compositions which comprise a therapeutically effective amount of a compound of Formula I or the pharmaceutically acceptable cationic and anionic salts, prodrugs and stereoisomers thereof and a pharmaceutically acceptable carrier.

This invention is also directed to pharmaceutical compositions for the treatment of hypercholesterolemia, hypertriglyceridemia, atherosclerosis, fungal infections, Alzheimer's or acne in a mammal (including a human) which comprise a therapeutically effective amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of hypercholesterolemia in a mammal (including a human being) which comprise a hypercholesterolemia treating amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of hypertriglyceridemia in a mammal (including a human being) which comprise a hypertriglyceridemia treating amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of atherosclerosis in a mammal (including a human being) which comprise an atherosclerosis treating amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of a fungal infection in a mammal (including a human being) which comprise an antifungal treating amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of Alzheimer's disease in a mammal (including a human being) which comprise an Alzheimer's disease treating amount of a compound of the Formula I or the pharmaceutically acceptable cationic and anionic salts, prodrugs and stereoisomers thereof and a pharmaceutically acceptable carrier.

This invention is also directed to pharmaceutical compositions for the treatment of acne in a mammal (including a human being) which comprise an acne treating amount of a compound of the Formula I or the pharmaceutically acceptable cationic and anionic salts, prodrugs and stereoisomers thereof and a pharmaceutically acceptable carrier.

Another aspect of this invention is a compound of the Formula I or the pharmaceutically acceptable cationic and anionic salts, prodrugs and stereoisomers thereof or a composition which comprises an amount thereof, for use as a medicament, in particular as an antifungal agent, hypocholesterolemic agent, hypotriglyceridemic agent, anti-atherosclerosis agent, anti-Alzheimer's disease agent or anti-acne agent.

Yet another aspect of this invention is the use of a compound of the Formula I or the pharmaceutically acceptable cationic and anionic salts, prodrugs and stereoisomers thereof or a composition which comprises an amount thereof, for the manufacture of an antifungal agent, hypocholesterolemic agent, hypoglyceridemic agent, anti-atherosclerosis agent, anti-Alzheimer's disease agent or anti-acne agent.

This invention is also directed to a pharmaceutical combination composition for the treatment of hypercholesterolemia comprising:

a therapeutically effective amount of a first compound, said first compound being a compound of Formula I or the pharmaceutically acceptable cationic and anionic salts, prodrugs and stereoisomers thereof;

a therapeutically effective amount of a second compound, said compound being a cholesterol absorption inhibitor, a cholesterol synthesis inhibitor (other than the compounds of Formula I), a fibrate, niacin, an ion-exchange resin, an antioxidant, an ACAT inhibitor or a bile acid sequestrant; and a pharmaceutical carrier.

Preferred among the second compounds are an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin or rivastatin.

A particularly preferred lanosterol demethylase inhibitor is fluconazole or voriconazole.

Another aspect of this invention is a method for treating hypercholesterolemia in a mammal comprising administering to a mammal suffering from hypercholesterolemia a therapeutically effective amount of a first compound, said first compound being a compound of Formula I or the pharmaceutically acceptable cationic and anionic salts, prodrugs and stereoisomers thereof; and a therapeutically effective amount of a second compound, said second compound being a cholesterol absorption inhibitor or a cholesterol synthesis inhibitor (other than the compounds of Formula I), a fibrate, niacin, an ion-exchange resin, an antioxidant, an ACAT inhibitor or a bile acid sequestrant.

A preferred aspect of the above method is wherein the second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred aspect of the above method is wherein the HMG-CoA reductase inhibitor is lovastatin, simvastatin, pravastatin, fluvastatin, atorvastatin or rivastatin.

Yet another aspect of this invention is a kit containing a treatment for hypercholesterolemia comprising:

a. a therapeutically effective amount of a first compound, said first compound being a compound of Formula I or the pharmaceutically acceptable cationic and anionic salts, prodrugs and stereoisomers thereof and a pharmaceutically acceptable carrier in a first unit dosage form;

b. a therapeutically effective amount of a second compound, said second compound being a cholesterol absorption inhibitor, a cholesterol synthesis inhibitor (other than the compounds of Formula I), a fibrate, niacin, an ion-exchange resin, an antioxidant, an ACAT inhibitor or a bile acid sequestrant and a pharmaceutically acceptable carrier in a second unit dosage form; and c. container means for containing said first and second dosage forms.

A preferred second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin or rivastatin.

This invention is also directed to a pharmaceutical combination composition for the treatment of a fungal infection comprising:
a therapeutically effective amount of a compound of Formula I or the pharmaceutically acceptable cationic and anionic salts, prodrugs and stereoisomers thereof;
a therapeutically effective amount of a lanosterol demethylase inhibitor; and
a pharmaceutical carrier.

A particularly preferred lanosterol demethylase inhibitor is fluconazole.

Another particularly preferred lanosterol demethylase inhibitor is voriconazole.

Another aspect of this invention is a method for treating a fungal infection in a mammal comprising administering to a mammal suffering from a fungal infection
a therapeutically effective amount of a compound of Formula I or the pharmaceutically acceptable cationic and anionic salts, prodrugs and stereoisomers thereof; and
a therapeutically effective amount of a lanosterol demethylase inhibitor.

A particularly preferred aspect of the above method is wherein the lanosterol demethylase inhibitor is fluconazole.

Another particularly preferred aspect of the above method is wherein the lanosterol demethylase inhibitor is voriconazole.

Yet another aspect of this invention is a kit containing a treatment for a fungal infection comprising:

a. a therapeutically effective amount of a compound of Formula I or the pharmaceutically acceptable cationic and anionic salts, prodrugs and stereoisomers thereof and a pharmaceutically acceptable carrier in a first unit dosage form;

b. a therapeutically effective amount of a lanosterol demethylase inhibitor and a pharmaceutically acceptable carrier in a second unit dosage form; and c. container means for containing said first and second dosage forms.

A particularly preferred aspect of the above kit is wherein the lanosterol demethylase inhibitor is fluconazole.

Another particularly preferred aspect of the above kit is wherein the lanosterol demethylase inhibitor is voriconazole.

This invention is also directed to a pharmaceutical combination composition for the treatment of acne comprising:
a therapeutically effective amount of a compound of Formula I or the pharmaceutically acceptable cationic and anionic salts, prodrugs and stereoisomers thereof;
a therapeutically effective amount of an antibiotic agent; and
a pharmaceutical carrier.

Another aspect of this invention is a method for treating acne in a mammal comprising administering to a mammal suffering from acne
a therapeutically effective amount of a compound of Formula I or the pharmaceutically acceptable cationic and anionic salts, prodrugs and stereoisomers thereof; and
a therapeutically effective amount of an antibiotic agent.

Yet another aspect of this invention is a kit containing a treatment for acne comprising:

a. a therapeutically effective amount of a compound of Formula I or the pharmaceutically acceptable cationic and anionic salts, prodrugs and stereoisomers thereof and a pharmaceutically acceptable carrier in a first unit dosage form;

b. a therapeutically effective amount of an antibiotic agent and a pharmaceutically acceptable carrier in a second unit dosage form; and c. container means for containing said first and second dosage forms.

The term "treating", "treat" or "treatment" as used herein includes preventative (e.g., prophylactic) and palliative treatment.

Although the naphthyl substituents $R_3$, $R_9$ and $R_{20}$ are depicted in Formula I as connected to a particular side of the naphthyl ring, each substituent may independently be substituted on one side of the naphthyl ring or the other.

Exemplary T rings are piperidin-1-yl, pyrrolidin-1-yl, thiazolidin-3-yl, azetidin-1-yl, tetrahydro-1,4-thiazin-4-yl, tetrahydro-1,4-oxazin-4-yl and tetrahydro-1,3-thiazin-3-yl.

Exemplary U rings are cyclopropyl, cyclobutyl, cyclopentyl and cyclohexyl.

Exemplary het rings are pyrazolyl, imidazolyl, triazolyl, tetrazolyl, piperidinyl, piperazinyl or morpholino.

By halo is meant chloro, bromo, iodo, or fluoro.

By alkyl is meant straight chain or branched saturated hydrocarbon.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, L-lysine, L-arginine, meglamine (N-methyl-glucamine), benethamine (N-benzylphenethylamine), piperazine or tromethamine (2-amino-2-hydroxymethyl-1,3-propanediol). This is meant to include (R)-a-methylbenzylammonium.

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the Formula I compounds include but are not limited to substituents wherein the Z, V or $V_1$ moiety is independently carboxyl and the free hydrogen is replaced by $(C_1-C_4)$alkyl, $(C_2-C_7)$ alkanoyloxymethyl, 1-(alkanoyloxy)ethyl having from 4 to 9 carbon atoms, 1-methyl-1-(alkanoyloxy)—ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, N-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as γ-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, the expression "reaction-inert solvent" and inert solvent refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included as an aspect of this invention.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

Other features and advantages will be apparent from the specification and claims which describe the invention.

DETAILED DESCRIPTION OF THE INVENTION

In general the compounds of this invention can be made by processes which include processes known in the chemical arts, particularly in light of the description contained herein. Certain processes for the manufacture of the compounds of this invention are provided as further features of the invention and are illustrated by the following reaction schemes.

Reaction Scheme 1

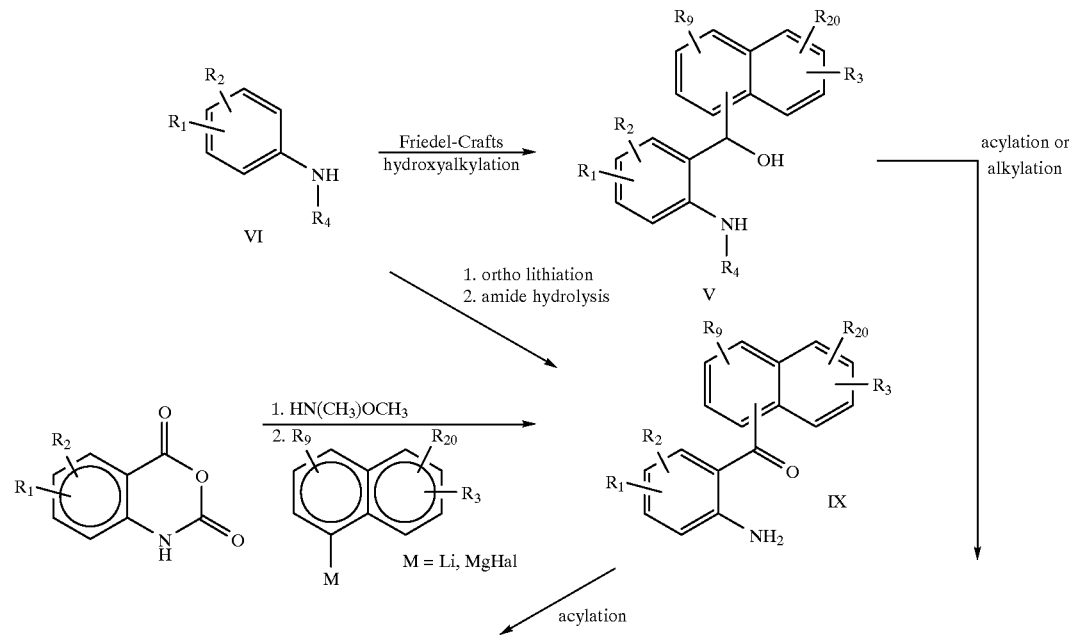

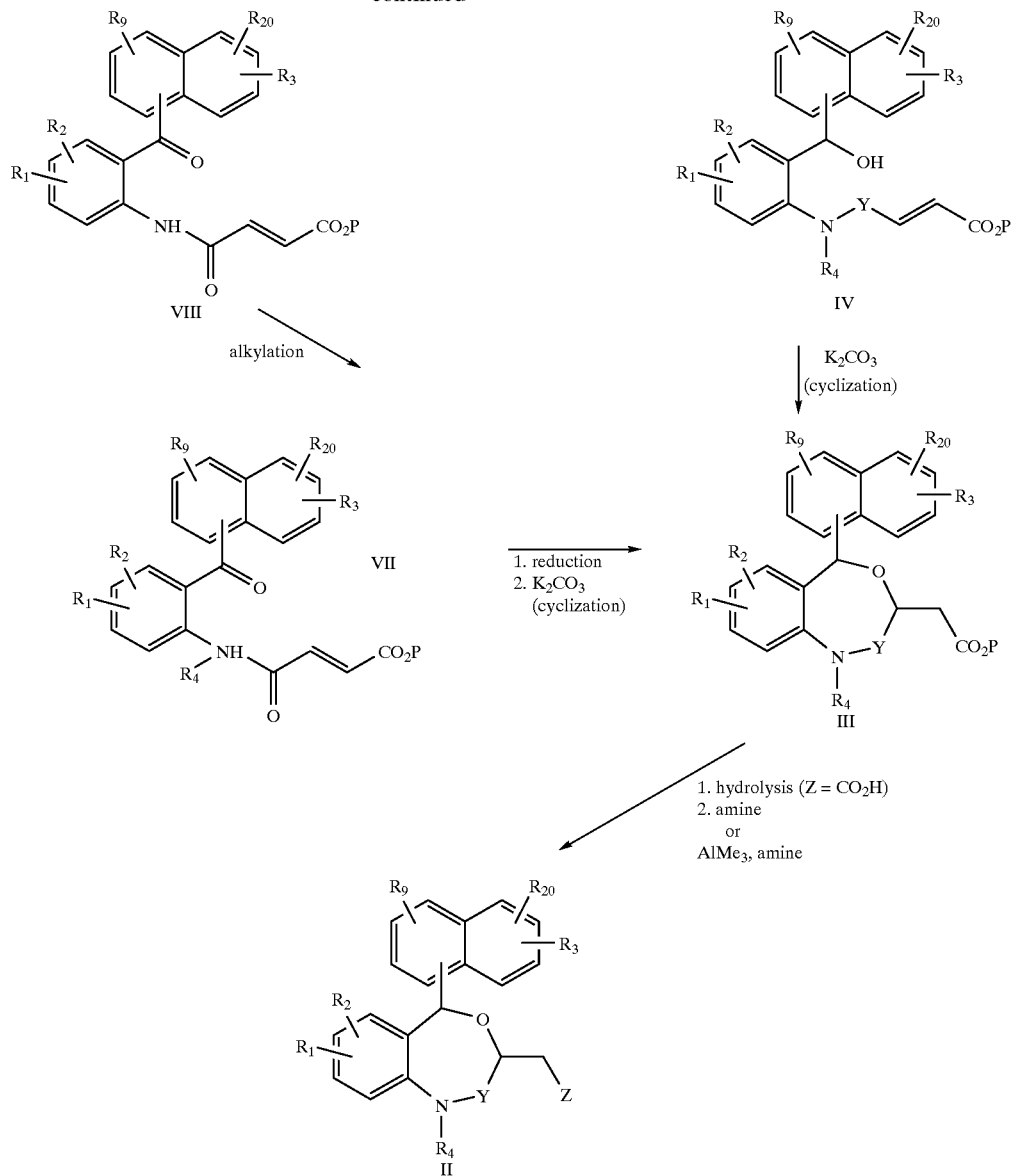

Reaction Scheme 2

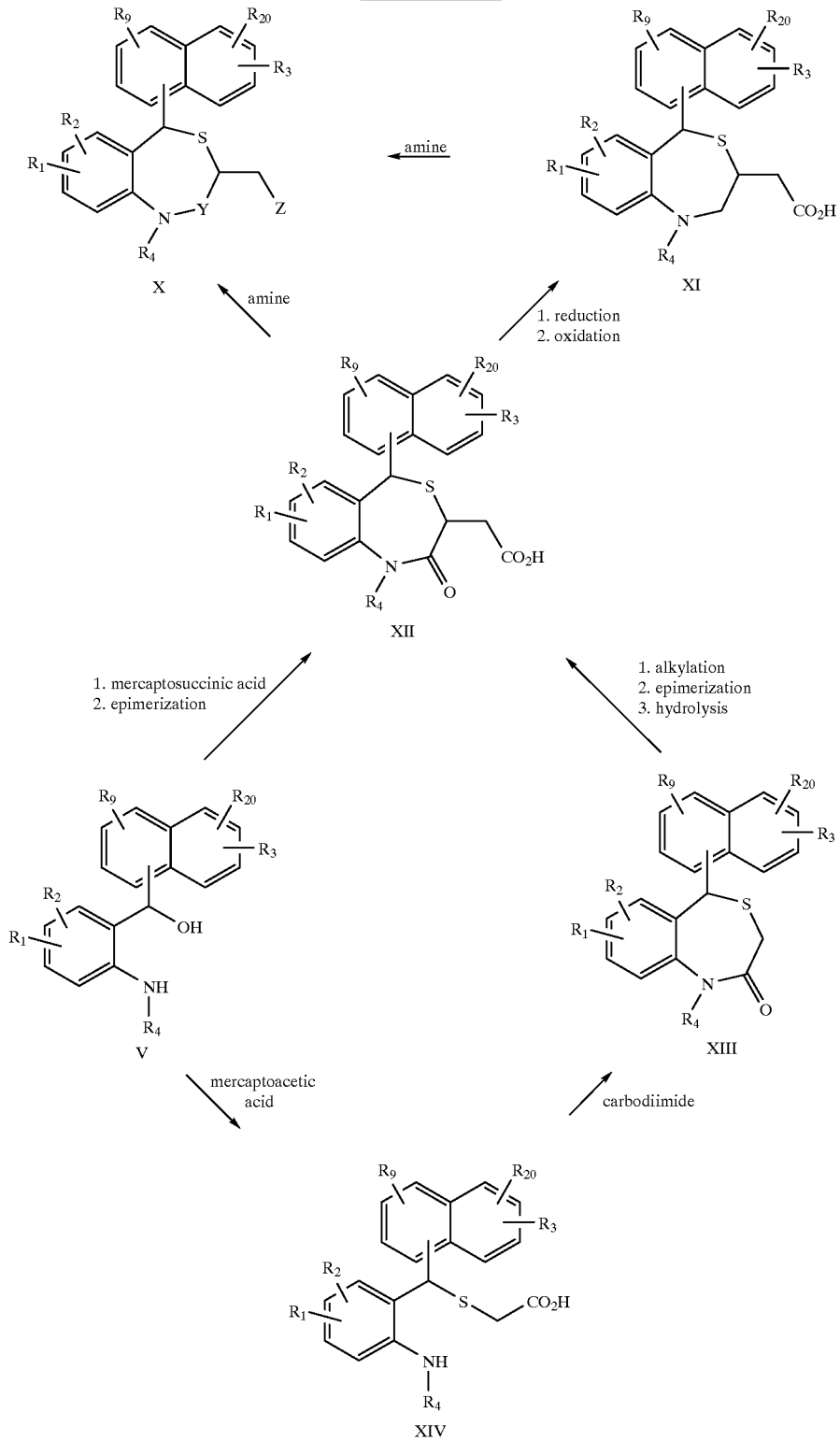

As a preliminary note, some substituents (e.g., $R_4$) may best be prepared through conversion of another functional group at a point later in the synthetic sequence to the introduction of the substituents (e.g., $R_4$ in Formulas VI and VII). When to use these conversion methods sill vary depending on the nature of the substituent and the compound's stability to the reaction conditions and can be readily determined by one skilled in the art. The method of preparation can also be readily determined by one skilled in the art using conventional methods of organic synthesis.

Also, some of the preparation methods described herein will require protection of remote functionality (i.e., carboxyl, hydroxyl). The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$)alkoxymethyl, arylmethyl and tri($C_1$–$C_4$)alkylsilyl) and their use, see T. W. Greene, *Protective Groups in Organic Synthesis*, John Wiley & Sons, New York, 1991.

According to Reaction Scheme 1 the desired Formula I compounds wherein $R_1$, $R_2$, $R_3$, $R_4$, $R_{20}$ and $R_9$ are as described above, X is oxy, Y is carbonyl or methylene and Z is a substituted amide (depicted as Formula II compounds) may be prepared by acylating the appropriate amine with the corresponding Formula III compound wherein P is hydrogen (Z is carboxyl in Formula II compounds). The Formula III compound wherein P is hydrogen may be prepared from the corresponding Formula III compound wherein P is a known carboxyl protecting group (see reference above) by hydrolysis. Alternatively, the hydrolysis step may be omitted resulting in the desired prodrugs of Formula II compounds where Z is carboxyl.

Generally, a Formula III compound where P is a known carboxyl protecting group is hydrolyzed in an aqueous alcoholic solvent such as methanol/water with a base such as potassium carbonate at a temperature of about 40° C. to about 80° C., preferably at reflux, for about 2 hours to about 18 hours to provide a Formula II compound wherein Z is carboxyl. The acid is then combined with the appropriate amine in an aprotic solvent such as dimethylformamide in the presence of an amine base such as triethylamine and a coupling agent such as diethyl cyanophosphonate or propylphosphonic anhydride at a temperature of about 0° C. to about 40° C. for about 1 hour to about 6 hours.

Alternatively, the acid is combined with the appropriate amine in the presence of a carbodiimide (e.g., 1-(3-dimethylaminopropyl)-3-ethylcarbodiimide hydrochloride) in a reaction inert solvent such as methylene chloride at a temperature of about 10° C. to 40° C. for about 2 to about 24 hours.

The desired Formula I compound wherein Z or V is tetrazol-5-yl may be prepared from the corresponding Formula I compound wherein Z or V is carboxyl by converting the carboxyl group to a carboxamide group (Z or V is $CONH_2$), dehydrating the carboxamide to the nitrile (Z or V is CN) and reacting the nitrile with an appropriate azide to form the desired tetrazole group.

Generally, the acid is converted to the imidazolide by reaction with carbonyl diimidazole in an aprotic solvent such as methylene chloride at a temperature of 15° C. to about 40° C. for about 30 minutes to about 4 hours, conveniently at room temperature for 1 hour. The resulting imidazolide is converted to the corresponding amide by bubbling ammonia gas into the reaction mixture at a temperature of 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at 0° C. for about 25 minutes to 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula I compound wherein Z or V is 4,5-dihydro-5-oxo-1,2,4-oxadiazol-3-yl may be prepared from the corresponding Formula I compound wherein Z or V is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to 24 hours, preferably in refluxing ethanol for about 18 hours. The amide oxime is converted to the corresponding 4,5-dihydro-5-oxo-1,2,4-oxadiazole derivative by reaction with carbonyldiimidazole and triethylamine in refluxing ethyl acetate for 24 hours.

The desired Formula I compound wherein Z is aminocarbonyl or (di)alkylaminocarbonyl may be prepared from the corresponding Formula III compound where P is alkyl by reaction with a complex of an amine salt and trimethylaluminum in an inert solvent such as toluene at a temperature of about 25° C. to 110° C. for about 2 to 24 hours. When the amine is ammonia, the reaction may yield either the nitrile or the carboxamide. The nitrile may be hydrolyzed to the primary carboxamide (Z or V=$CONH_2$) by treatment with aqueous hydrogen peroxide in the presence of a base such as potassium carbonate in a cosolvent such as ethanol or dimethylsulfoxide at a temperature of 10° C. to 100° C. for about 2 to 24 hours. Alternatively, the Formula I compound wherein Z is aminocarbonyl or (di)alkylaminocarbonyl may be prepared by converting the acid to its imidazolide followed by conversion to the amide as described above for the preparation of the Formula I compounds wherein Z or V is tetrazol-5-yl.

Prodrugs of Formula I compounds having a carboxyl group may be prepared by combining the acid with the appropriate alkyl halide in the presence of a base such as potassium carbonate in an inert solvent such as dimethylformamide at a temperature of about 15° C. to about 100° C. for about 1 hour to about 24 hours.

Alternatively, the acid is combined with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula III compounds wherein $R_1$, $R_2$, $R_3$, $R_4$, $R_{20}$ and $R_9$ are as described above, X is oxy, Y is carbonyl or methylene and P is a known carboxyl protecting group (see reference above) may be prepared from the corresponding Formula IV compound by cyclization.

Generally, the Formula IV compound is combined with a base such as potassium carbonate in an alcoholic solvent such as ethanol at a temperature of about 10° C. to about 40° C., preferably ambient temperature, for about 2 hours to about 18 hours.

The desired Formula IV compounds wherein $R_1$, $R_2$, $R_3$, $R_4$, $R_{20}$ and $R_9$ are as described above, X is oxy, Y is carbonyl or methylene and P is a known carboxyl protecting group (see reference above) may be prepared from the appropriate corresponding Formula V compound by acylation or alkylation as appropriate.

Generally, for those compounds wherein Y is carbonyl the appropriate Formula V compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours. Generally, for those compounds wherein Y is methylene the appropriate Formula V compound is combined with the appropriate protected 4-halocrotonic acid, such as alkyl 4-halocrotonate, in the presence of a base such as potassium carbonate in a polar aprotic solvent such as dimethylformamide at a temperature of about 10° C. to about 50° C., typically ambient, for about 12 hours to about 72 hours.

The $R_4$ substituent may be added to either the Formula VI or Formula V compounds by the following three alternative methods.

The desired Formula V compound wherein $R_1$, $R_2$, $R_3$, $R_4$, $R_{20}$ and $R_9$ are as described above may be prepared from the appropriate corresponding Formula VI compound by hydroxyalkylation (a modified Friedel-Crafts reaction).

Generally, the Formula VI compound is combined with a Lewis acid such as boron trichloride in a reaction-inert solvent such as benzene or toluene at a temperature of about ambient to about reflux for about 1 to about 6 hours under a nitrogen atmosphere to form an intermediate complex. The resulting complex is combined with the appropriately substituted naphthaldehyde in a reaction-inert solvent such as benzene in the presence of an amine base such as triethylamine at a temperature of about 0° C. to about 40° C., typically ambient, for about 30 minutes to about 18 hours followed by aqueous acid cleavage of the boron moiety.

Alternatively, a Formula V compound wherein $R_1$, $R_2$, $R_3$, $R_4$, $R_{20}$ and $R_9$ are as described above may be prepared by treating the corresponding Formula VI compound wherein $R_4$ is alkanoyl, optionally substituted as described above, with excess strong base, preferably 2.5 equivalents of n-butyllithium, in an anhydrous ethereal solvent, preferably tetrahydrofuran. The reaction is performed at a temperature of 0° C. to about 50° C. for about 1 hour to about 3 hours and the resulting dianion is reacted with the appropriate naphthaldehyde. The resulting substituted phenylnaphthalenylmethanol compound, is then reacted with a reducing agent, such as a borane-dimethyl sulfide complex, in an ethereal solvent, such as tetrahydrofuran, at an elevated temperature, typically reflux, resulting in the corresponding amine (optionally substituted as described above for $R_4$ ).

In yet another alternative method, the Formula V compounds wherein $R_1$, $R_2$, $R_3$, $R_4$, $R_{20}$ and $R_9$ are as described above may be prepared by treating the Formula VI compound, wherein $R_4$ is alkoxycarbonyl, with excess strong base, preferably 2.4 equivalents of t-butyllithium, at a temperature of about –80° C. to about 0° C. The reaction is performed in an anhydrous ethereal solvent such as tetrahydrofuran for about 2 hours to about 4 hours and the resulting dianion is reacted with the appropriate naphthaldehyde. The resulting substituted phenylnaphthalenylmethanol compound is treated with aqueous acid and thereby converted to the Formula V compound, wherein $R_4$ is hydrogen. This compound is transformed to the Formula V compound, wherein $R_4$ is alkyl (optionally substituted as described above), by reductive amination under conditions analogous to those described (below) for the preparation of the Formula VI compounds.

The desired Formula VI compounds wherein $R_1$ and $R_2$ are as described above and $R_4$ is alkoxycarbonyl may be prepared by acylation of the corresponding aniline with the appropriate alkyl chloroformate in a manner similar to that used in preparation of Formula IV compounds wherein Y is carbonyl.

The desired Formula VI compound wherein $R_1$, $R_2$ and $R_4$ are as described above may be prepared from the appropriate corresponding aniline by reductive amination.

Generally, the aniline is reacted with the appropriate alkylaldehyde in a protic acidic solvent such as concentrated acetic acid at a temperature of about 10° C. to about 50° C., preferably ambient, for about 30 minutes to about four hours followed by reduction using for example sodium borohydride at a temperature of about 0° C. to about 20° C. for about 15 minutes to about four hours.

Alternatively, the aniline is reacted with the appropriate alkylaldehyde in an aprotic solvent such as 1,2-dichloroethane in the presence of an acid such as acetic acid at a temperature of about 15° C. to about 40° C., preferably ambient temperature, for a period of about 1 to about 20 hours. The resulting compound is reduced using for example, sodium triacetoxyborohydride at about –20° C. to about ambient temperature for a period of about 1 to about 20 hours.

Alternatively, the desired Formula III compounds wherein $R_1$, $R_2$, $R_3$, $R_4$, $R_{20}$ and $R_9$ are as described above, X is oxy, Y is carbonyl and P is a known carboxyl protecting group (see reference below) may also be prepared from the corresponding Formula VII compounds by reduction followed by cyclization.

Generally, the Formula VII compound is combined with a reducing agent such as sodium borohydride in methanol at a temperature of 0° C. to 30° C. for about 15 minutes to about 1 hour. The resulting compound is cyclized with a base such as potassium carbonate in an alcoholic solvent such as ethanol at a temperature of about 10° C. to about 40° C., preferably ambient, for about 2 hours to about 18 hours.

The desired Formula VII compounds wherein $R_1$, $R_2$, $R_3$, $R_4$, $R_{20}$ and $R_9$ are as described above, X is oxy, Y is carbonyl and P is a known carboxyl protecting group (see reference below) may be prepared from the appropriate corresponding Formula VIII compound by alkylation.

Generally, the Formula VIII compound is deprotonated with a base such as sodium hydride in a polar aprotic solvent such as dimethylformamide under a nitrogen atmosphere at a temperature of about 0° C. to about 50° C., for about 30 minutes to about 2 hours. Then the appropriate alkyl halide (e.g., $R_4$ halide) is added at a temperature of about 0° C. to about 60° C., typically ambient temperature, and reacted for about 30 minutes to about 24 hours.

The desired Formula VIII compounds wherein $R_1$, $R_2$, $R_3$, $R_{20}$ and $R_9$ are as described above, X is oxy, Y is carbonyl and P is a known carboxyl protecting group (see reference below) may be prepared from the appropriate corresponding Formula IX compound by acylation.

Generally, the appropriate Formula IX compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours.

The desired Formula IX compounds wherein $R_1$, $R_2$, $R_3$, $R_{20}$ and $R_9$ are as described above may be prepared from the appropriate corresponding Formula VI compound wherein $R_4$ is alkoxycarbonyl by directed ortho lithiation followed by hydrolysis of the amide.

Generally, the appropriate Formula VI compound where $R_4$ is alkoxycarbonyl is treated with excess strong base, preferably greater than 2 equivalents of secbutyllithium or tert-butyllithium, in an anhydrous ethereal solvent, preferably tetrahydrofuran, under a nitrogen atmosphere at a temperature of –40° C. to 10° C., preferably 0° C., for about 1 hour to about 5 hours. The resulting dianion is then reacted with a Weinreb amide of the appropriate naphthoic acid at a temperature of –100° C. to 0° C., preferably –78° C., for about 30 minutes to about 24 hours while gradually warming to ambient temperature. The resulting naphthophenone is treated with aqueous acid such as hydrochloric acid in a cosolvent such as tetrahydrofuran or dimethoxyethane at a temperature of 25° C. to 100° C., preferably at reflux, for about 5 hours to about 48 hours.

Alternatively the desired Formula IX compounds may be prepared from the corresponding isatoic anhydride by conversion to the Weinreb amide which is condensed with the appropriate metallated naphthalene derivative.

Generally the isatoic anhydride is reacted with O,N-dimethylhydroxylamine hydrochloride in the presence of a base such as triethylamine in water and a cosolvent such as dioxan or ethanol at a temperature of 50° C. to 100° C., preferably at reflux for about 1 to 5 hours. The Weinreb amide is deprotonated by a strong base such as butyllithium under a nitrogen atmosphere in an inert solvent such as tetrahydrofuran at a temperature of −78° C. to −40° C. for about 0.5 to 2 hours, then treated with a solution of the appropriate metallated, typically lithiated, naphthyl derivative in an inert solvent such as diethyl ether at a temperature of −100° C. to 0° C., preferably −78° C., for about 0.5 hours to about 24 hours (while gradually warming to 25° C.).

According to Reaction Scheme 2 the desired Formula X compounds wherein $R_1$, $R_2$, $R_3$, $R_4$, $R_{20}$ and $R_9$ are as described above, X is thio, Y is carbonyl or methylene and Z is a substituted amide may be prepared by acylating the appropriate amine with the corresponding Formula XI or XII compound. Generally this reaction may be performed as describe above for the Formula II compounds.

The desired Formula XI compound wherein $R_1$, $R_2$, $R_3$, $R_4$, $R_{20}$ and $R_9$ are as described above, X is thio and Y is methylene may be prepared from the appropriate corresponding Formula XII compound where Y is carbonyl by a sequential reduction/oxidation procedure.

Generally the Formula XII compound is fully reduced using for example a borane-methyl sulfide complex in a reaction-inert solvent such as tetrahydrofuran at a temperature of about 20° C. to about 80° C., preferably at ambient, for about 1 hour to about 24 hours. The resulting alcohol is then oxidized to the Formula XI compound using for example a two step procedure involving first a Swern oxidation followed by oxidation with buffered sodium chlorite in acetonitrile and aqueous hydrogen peroxide at a temperature of about −10° C. to about 25° C. for about 30 minutes to about 4 hours. Or alternatively, the alcohol is directly oxidized to the acid using t-butyl hydroperoxide and cetyl trimethyl ammonium sulfate in an aqueous mixture at pH greater than 13.

The desired Formula XII compound wherein $R_1$, $R_2$, $R_3$, $R_4$, $R_{20}$ and $R_9$ are as described above, may be prepared from the appropriate corresponding Formula XIII compound by alkylation followed by epimerization and finally hydrolysis.

Generally, the Formula XIII compound is combined with a base such as lithium diisopropylamide in a reaction-inert solvent such as cyclohexane/tetrahydrofuran at a temperature of about −100° C. to about −20° C. under nitrogen for about 30 minutes to about 3 hours followed by addition of a suitable alkyl haloacetate such as t-butyl bromoacetate and mixing for about 2 to about 24 hours at a temperature of about 10° C. to about 40° C., preferably ambient. The alkylated product is epimerized to exclusively the trans isomers using a base such as potassium carbonate in an alcoholic solvent like methanol for 1 hour to 6 hours at a temperature of about 40° C. to about 80° C., preferably at 60° C. The resulting alkyl ester may be hydrolyzed by treatment with an acid such as trifluoroacetic acid in a reaction-inert solvent such as dichloromethane.

The desired Formula XII compound wherein $R_1$, $R_2$, $R_3$, $R_4$, $R_{20}$ and $R_9$ are as described above, may be prepared from the appropriate corresponding Formula XIV compound by coupling under carbodiimide conditions.

Generally, the Formula XIV compound is combined with a suitable carbodiimide such as 1-(3-dimethylaminopropyl)-3-ethylcarbodiimide hydrochloride in a reaction-inert solvent such as dichloromethane at a temperature of about 10° C. to about 50° C., conveniently at ambient temperature, for about 5 hours to about 24 hours.

The desired Formula XIV compound wherein $R_1$, $R_2$, $R_3$, $R_4$, $R_{20}$ and $R_9$ are as described above, may be prepared from the appropriate corresponding Formula V compound by a solvolytic displacement reaction.

Generally, the Formula V compound may be combined with mercaptoacetic acid under aqueous acidic conditions at a temperature of about 60° C. to about 120° C., conveniently at reflux, for about 2 to about 6 hours.

Alternatively, the desired Formula XII compounds wherein $R_1$, $R_2$, $R_3$, $R_4$, $R_{20}$ and $R_9$ are as described above may be prepared from the appropriate corresponding Formula V compound by a solvolytic displacement reaction with mercaptosuccinic acid, cyclization to the lactam, and epimerization.

Generally, the Formula V compound and mercaptosuccinic acid are combined in a carboxylic acid solvent such as propionic acid with a means to remove water, such as a nitrogen sweep across the head space of the reaction vessel, and heated to about 100° C. to about 140° C. for about 12 to 72 hours. The cyclized product is epimerized to the trans isomers by treatment in an inert solvent such as tetrahydrofuran with a base, such as a metal alkoxide base, in the corresponding alcohol solvent, preferably sodium methoxide in methanol, at about ambient temperature to reflux temperature for a period of about 1 to about 24 hours.

It is reiterated that some substituents (e.g., $R_4$) may best be prepared through conversion of another functional group at a point later in the synthetic sequence to the introduction of the substituents (e.g., $R_4$ in Formulas VI and VII). When to use these conversion methods will vary depending on the nature of the substituent and the compound's stability to the reaction conditions and can be readily determined by one skilled in the art. The method of preparation can also be readily determined by one skilled in the art using conventional methods of organic synthesis.

Alternatively, the compounds of this invention may be prepared by biotransformation as described generally hereinafter and more particularly in the Examples.

Generally, the compounds of this invention may be prepared by contacting the substance to be transformed, and other necessary reactants, with the enzymes derived from a variety of living organisms under conditions suitable for a chemical interaction to occur. Subsequently, the products of the reaction are separated and those of interest are purified for elucidation of their chemical structure and physical and biological properties. The enzymes can be present as purified reagents, be in crude extracts or lysates, or be in intact cells and can be in solution, be in suspension (e.g., intact cells), be covalently attached to a supporting surface, or be imbedded in a permeable matrix (e.g., agarose or alginate beads). The substrate and other necessary reactants (e.g., water, air) are supplied as the chemistry dictates. Generally, the reaction is carried out in the presence of one or more liquid phases, aqueous and/or organic, to promote mass transfer of the reactants and products. The reaction can be conducted aseptically or not. The conditions for monitoring the progress of the reaction and the isolation of the products of the reaction varies according to the physical properties of the reaction system and the chemistry of the reactants and products.

A general exemplary process to prepare the compounds of this invention is described as follows. Nutrient medium (e.g., IOWA Medium: dextrose, yeast extract, dipotassium hydrogen phosphate, sodium chloride, soybean flour, water; adjusted to neutral pH) is added to one or more culture vessels (e.g., fermentation tubes or flasks) which are then steam-sterilized. Each vessel is aseptically inoculated with growth from an agar culture, a suspension of washed cells or spores, or broth from a liquid nutrient medium culture of the biotransforming microorganism. The vessels are mounted on a shaker designed for fermentation and shaken (e.g., 100–300 rpm) at an appropriate temperature (e.g., 20–40° C.) long enough to promote the growth of the microorganism to a suitable population size (e.g., 1–3 days). The substrate to be transformed is dissolved in a suitable water-miscible solvent (e.g., dimethylsulfoxide, dimethylformamide, ethyl alcohol) and sterilized by membrane filtration. To each of the biotransformation vessels, the resulting solution is aseptically added to achieve the desired concentration of substrate (e.g., 100–200 mcg/mL). The dosed vessels are mounted on the shaker and shaken as before, until the substrate has been converted to product[s] by microbial metabolism (e.g., 1–10 days). The contents of the biotransformation vessel are extracted with a suitable water-immiscible solvent (e.g., ethyl acetate, chloroform, methylene chloride). The solvent layers from the extraction are recovered, combined, and concentrated to dryness under reduced pressure. The dried crude is redissolved in a solvent that is compatible with the purification method (e.g., acetonitrile, methanol, or HPLC method mobile phase) and purified by reversed-phase high performance liquid chromatography (HPLC). The biotransformation product[s] are monitored during chromatographic separation by UV-absorbance and photodiode array profile. Fractions of the HPLC mobile phase containing the product[s] of interest are retained and the product[s] are extracted from the mobile phase with a suitable water-immiscible solvent (e.g., ethyl acetate, chloroform, methylene chloride). The solvent layers from the extraction are recovered, dried over anhydrous sodium sulfate or anhydrous magnesium sulfate, filtered to remove solids, and concentrated under reduced pressure to produce dried purified biotransformation product[s]. The chemical structure of the isolated product[s] is determined from the data derived from mass spectroscopy and $^1$H-NMR.

The starting materials and reagents for the above described reaction schemes (e.g., 4-haloaniline, 1-naphthaldehyde, furmaric acid monoethyl ester, amino acid esters, prodrug residues, protected forms) are readily available or can be easily synthesized by those skilled in the art using conventional methods of organic synthesis. The preparation of certain compounds disclosed in PCT Publication WO 96/09827 may be used as an aid in preparing the certain starting materials. In addition, some of the intermediates used herein to prepare the compounds of this invention are, or are related to, or are derived from amino acids found in nature, in which there is a large scientific interest and commercial need, and accordingly many such intermediates are commercially available or are reported in the literature or are easily prepared from other commonly available substances by well known methods which are reported in the literature.

The methods described above are useful to prepare the compounds of this invention, other methods may be described in the experimental section.

The compounds of Formula I have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture (e.g., ester or salt) by reaction with an appropriate optically active compound (e.g., alcohol or amine), separating the diastereomers and converting (e.g., hydrolyzing or acidifying) the individual diastereomers to the corresponding pure enantiomers. All such isomers, including diastereomers and enantiomers are considered as part of this invention.

Some of the compounds of this invention, where for example Z contains an acid group, are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention where, for example Y is methylene or Z contains an amine group are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The utility of the compounds of the present invention as medical agents in the treatment of diseases (such as are detailed herein) in mammals (e.g., humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

The compounds of this invention are all adapted to therapeutic use as agents that lower plasma LDL cholesterol levels in mammals, particularly humans. Since the concentration of cholesterol in blood is closely related to the development of cardiovascular, cerebral vascular or peripheral vascular disorders, these compounds, by virtue of their hypocholesterolemic action, prevent, arrest and/or regress atherosclerosis.

The hypocholesterolemia activity of these compounds can be determined by assessing the effect of these compounds on the action of squalene synthetase by measuring the overall conversion of [1-$^3$H]farnesyl pyrophosphate ([$^3$H]FPP) to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A).

Briefly, to a 3 µl volume of either DMSO (control) or DMSO containing compound, are added 47 µl of Squalene Synthetase Cofactor/Substrate solution (SQS Cofactor/Substrate solution contains 50 mM K$_x$PO$_4$ (pH 7.4), 5.0 mM MgCl$_2$, 411 µM NADP$^+$, 3.4 mM glucose-6-phosphate, 20 U/ml glucose-6-phosphate dehydrogenase, 15 mM NaF, 78.1 mM sodium ascorbate, 31.3 U/ml ascorbate oxidase, and 1.56 times the indicated final concentrations of [$^3$H]FPP (sp. act. 380/pmol)) and 25 µl of PMED buffer (PMEB buffer contains 50 mM K$_x$PO$_4$ (pH 7.4), 5 mM MgCl$_2$, 1.0 mM EDTA, 5.0 mM dithiothreitol) containing 1 mg/ml microsomal protein [Final assay concentrations: 48 mM K$_x$PO$_4$ (pH 7.4), 4.8mM MgCl$_2$, 0.33 mM EDTA, 1.67 mM DTT, 258 µM NADP$^+$, 2.1 mM glucose-6-phosphate, 0.95U glucose-6-phosphate dehydrogenase, 9.5 mM NaF, 50 mM sodium ascorbate, 1.5U ascorbate oxidase, 4% DMSO, and 5.1 μM [$^3$H]farnesyl pyrophosphate]. After incubation at 37° C. for 30 min, enzymatic reactions are terminated by sequential addition of 40 μl 10M NaOH, 40 μl EtOH, 10 μl of 2 mg/ml squalene in chloroform. After saponification (90 minutes, 37° C.), aliquots were applied to silica gel TLC and newly formed squalene separated from unreacted substrate by chromatography in toluene-ethyl acetate (9:1). The squalene band is visualized with iodine vapors, removed, and immersed in Aqualsol-2 liquid scintillation fluid. Squalene synthetase activity is expressed as pmoles of squalene formed from farnesyl pyrophosphate per min of incubation at 37° C. per mg microsomal protein, based on the stoichiometry of the reaction whereby two moles of [$^3$H]farnesyl pyrophosphate react to form one mole of [$^3$H]squalene and half of the radiolabel is lost from the C-1 position of the prenylating [$^3$H]farnesyl pyrophosphate due to 1-pro-S hydrogen release. Rat hepatic microsomes are used as the source of squalene synthetase activity as described by Harwood et al (J. Lipid Res. 34, 377, 1993). Briefly, hepatic tissues are rinsed in phosphate buffered saline and immediately homogenized at 4° C. in PMED buffer, using a Dounce tissue homogenizer. Homogenates are centrifuged at 10,000×g for 20 min at 4° C. and the resultant supernatants are centrifuged at 178,000×g for 90 min at 4° C. Microsomal pellets are resuspended in PMED buffer by a Potter-Elvehjem pestle and stored frozen in liquid $N_2$ until use. For such preparations, there is no notable loss in enzyme activity within 3 months.

The hypercholesterolemic treating activity of these compounds may be demonstrated by methods based on standard procedures. For example, the in vivo activity of these compounds in inhibiting cholesterol biosynthesis may be determined by the procedure of Hughes et. al. 1977 J. Biol Chem. 252: 548.

Activity of these compounds can be determined by the amount of hypocholesterolemic agent that reduces hepatic cholesterol biosynthesis, relative to control, in male CD1 mice. Male CD1 mice are maintained on a cholesterol-free diet in a 12 hr light/12 hr dark cycle. At mid light cycle animals are administered a 0.5 mL oral bolus of saline containing 0.25% methyl cellulose, 0.6% Tween 80 and 10% ethanol (control animals) or an oral bolus that contained in addition the desired concentration of compound to be tested. One hour following bolus administration the animals receive an intraperitoneal injection (0.15 ml) of [$^{14}$C]-mevalonolactone dissolved in water (0.5 uCi/animal). One hour following the injection of radioactivity animals are sacrificed, livers excised, saponified ((2.5M KOH, 2 h) 60° C.) and extracted with petroleum ether and ethanol. After saponification, the radioactivity is measured. Total hepatic radioactivity is calculated based on measured liver weights. The degree of cholesterol biosynthesis inhibition is expressed as a percentage of the total radioactivity in treated vs control animals. The above assay carried out with a range of doses of test compounds allow the determination of an $ED_{50}$ value for the in vivo reduction of hepatic cholesterol biosynthesis.

The hypercholesterolemic and hypertriglyceremia treating activity of these compounds may also be demonstrated by determining the amount of agent required to reduce cholesterol levels and/or triglycerides. For example LDL cholesterol levels may be measured in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). Adult marmosets are assigned to treatment groups so that each group has a similar mean ±SD for total plasma cholesterol concentration. After group assignment, marmosets are dosed daily with compound as a dietary admix or by intragastric intubation for from one to eight weeks. Control marmosets receive only the dosing vehicle. Plasma total, LDL and HDL cholesterol values can be determined at any point during the study by obtaining blood from an antecubital vein and by separating plasma lipoproteins into their individual subclasses by density gradient centrifugation, and by measuring cholesterol concentration as previously described (Crook, et al., Arteriosclerosis 10, 625, 1990). An analogous measurement of triglycerides may be made to determine the effect on hypertriglyceremia using for example, an enzymatic assay kit (Wako Pure Chemical Industries).

Anti-atherosclerosis effects of the compounds can be determined by the amount of agent required to reduce the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean ±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention for the treatment of hypercholesterolemia, hypertriglyceridemia or atherosclerosis can be via any method which delivers the compound to the intestine and the liver. These methods include oral routes, parenteral, intraduodenal routes etc.

Thus, for example, in one mode of administration a compound of this invention may be administered once at night prior to sleep. Alternatively the compounds may be administered twice or three times daily with or without meals. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the compound to achieve the plasma cholesterol lowering that he/she considers appropriate for the patient. In considering the degree of hypocholesterolemic activity desired, the physician must balance a variety of factors such as starting cholesterol level, other cardiovascular risk factors, presence of preexisting disease, and age of the patient and his/her motivation. Those skilled in the art will know of the National Cholesterol Education program guidelines for treatment of hypercholesterolemia (Circulation 1991; 83:2154)

In general an effective dosage for the compounds described above for the treatment of hypercholesterolemia, hypertriglyceridemia or atherosclerosis is in the range of 0.0005 to 50 mg/kg/day, preferably 0.001 to 25 mg/kg/day, most preferably 0.005 to 5 mg/kg/day. For an average 70 kg human, this would amount to 0.000035 to 3.5 g/day, preferably 0.00007 to 1.75 g/day, most preferably 0.00035 to 0.35 g/day.

The compounds of this invention are also effective as antifungal agents, useful in the curative or prophylactic treatment of fungal infections in animals such as mammals, including humans. For example, they are useful in treating superficial fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, species of Candida (e.g. *Candida albicans*), *Cryptococcus neoformans, Aspergillus flavus, Aspergillus fumigatus*, Coccidioides, Paracoccidioides, Histoplasma or Blastomyces.

The in vitro evaluation of the antifungal activity of the compounds of this invention can be performed by determining the minimum inhibitory concentration (MIC), which is the concentration of the test compounds, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans*, and each plate is then incubated for 48 hours at 37° C. The plates are then examined for the presence or absence of growth of the fungus and the appropriate MIC value is noted. Other micro-organisms used in such tests can include *Candida Albicans, aspergillus fumigatus*, Trichophyton spp., Microsporum spp., *Epidermophyton floccosum, Coccidioides immitis* and *Torulopsis glabrata*.

The in vivo evaluation of the compounds as antifungal agents can be carried out at a series of dose levels by intraperitoneal or intravenous injection, or by oral administration, to mice or rats which are inoculated with, e.g. a strain of *Candida albicans, Aspergillus fumigatus* or *Cryptococcus neoformans*. Activity may be based on the number of survivors from a treated group of mice after the death of an untreated group of mice.

For Candida spp. infection models the dose level at which the compounds provides 50% protection against the lethal effect of the infection ($PD_{50}$) is also assessed.

For Aspergillus spp. infection models the number of mice cured of the infection after a set dose allows further assessment of activity.

For Cryptococcus spp. infection models the number of colony forming units existing after a set dose is assessed and compared with control to determine compound efficacy. A preliminary assessment of potential liver toxicity may also be made on the basis of increase in liver weight relative to control.

As an antifungal treatment the compounds of this invention are administered to mammals (e.g., humans) by conventional methods.

For human antifungal use, the compounds of this invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral antifungal administration to human patients, the daily dosage level of the compounds of this invention for antifungal treatments will be from 0.01 to 20 mg/kg, preferably 0.5 to 5 mg/kg, (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of this invention can be administered in the form of a suppository pessary, or they may be applied topically in the form of a lotion, solution, cream, ointment or dusting powder. For example, they can be incorporated into a cream consisting an aqueous emulsion of polyethylene glycols or liquid paraffin; or they can be incorporated, at a concentration between 1 to 10%, into an ointment comprising a white wax or white soft paraffin base together with such stabilizers and preservatives as may be required.

Since the compounds of this invention are cholesterol biosynthesis inhibitors they can also lower the levels of Apolipoprotein E isoform 4 circulating in the bloodstream. Apolipoprotein E isoform 4 that is made in the brain also circulates through the central nervous system and is present in the cerebrospinal fluid. Compounds of this invention are useful for the treatment of Alzheimer's disease.

Apolipoprotein E isoform 4 ("ApoE isoform 4") is an apolipoprotein which is the gene product of the apolipoprotein E Type 4 allele and is carried in the bloodstream on lipoproteins including LDL. Possession of one or two copies of the apolipoprotein E type 4 allele has been linked to a greatly increased risk of developing Alzheimer's disease. In the liver, low density lipoprotein receptors (LDL receptors) are responsible for absorbing and taking up from the bloodstream various lipoproteins including some of those containing ApoE isoform 4. LDL receptors are regulated by gene repressors derived from cholesterol that suppress the transcription of the LDL-receptor. Inhibition of cholesterol biosynthesis reduces the presence of these cholesterol-derived LDL gene repressors. This relieves the suppression of the production of the LDL receptor, leading to production of additional LDL receptors in the liver, which in turn, remove additional amounts of lipoproteins including ApoE Type 4 containing lipoproteins from the bloodstream. The Alzheimer's disease treating activity of these compounds can be determined by assessing the effect of these compounds on the action of squalene synthetase by measuring the overall conversion of [1-$^3$H]farnesyl pyrophosphate to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A). This assay is described more fully above.

The Alzheimer's disease treating activity of these compounds may also be demonstrated by determining the amount of agent required to reduce cholesterol levels, for example LDL cholesterol levels, in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). This assay is described more fully above.

The compounds of this invention may be administered using conventional methods for the treatment of Alzheimer's disease. In general an effective dosage for the squalene synthetase inhibitors of this invention for the treatment of Alzheimer's disease is in the range for adults of from about 1 mg to 1000 mg (preferably 5 to 100 mg,) which may be given in a single dose or in two to four divided doses. Higher doses may be favorably employed as required.

Since the compounds of this invention are squalene synthesis inhibitors they are effective for the treatment of acne vulgaris. Squalene is a major component of sebum, comprising about 12% of sebum in adults. The severity of acne vulgaris correlates directly with the sebum secretion rate and several compounds which decrease sebum secretion rate have been shown to improve acne. By inhibiting squalene the compounds of this invention can decrease the sebum secretion rate and thereby treat acne.

The concentration of squalene in sebum increases fourfold after puberty and it is believed that this increase in squalene concentration alone or in concert with other changes in sebum composition or sebum secretion rate facilitate the development of acne. The compounds of this invention are useful in preventing or mollifying acne by reducing the percentage and total amount of squalene in sebum.

In addition to reducing squalene levels in sebum, by limiting the production of epoxides, the sebum may become less inflammatory (through metabolic action of the ever-present P. acnes). The compounds of this invention may therefore provide a dual effect to combat acne and thus constitute a new, better treatment for acne than current keratolytic and anti-androgen therapies.

The anti-acne activity of the compounds of this invention may be demonstrated by testing the in vitro effects of the compounds in human sebaceous gland culture using conditions analogous to those described in FEBS Letters 200 (1), 173–176 (1986) and J. Cell Science 95, 125–136 (1990). Thus, the human sebaceous gland culture may be incubated with the test compound and subsequent sebum production and qualitative changes of sebum composition measured over a short period of time and compared with controls and other actives.

For the treatment of acne the compounds of this invention may be administered by conventional methods. For the treatment of acne each dosage unit will preferably contain 0.001 mg to 1000 mg, advantageously 0.01 mg to 400 mg, of active ingredient. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient.

The compounds of this invention may also be used in conjunction with other pharmaceutical agents. For example, they may be used in combination with other cholesterol synthesis inhibitors and cholesterol absorption inhibitors as described below and other cholesterol lowering agents such as fibrates, niacins, ion-exchange resins, antioxidants, ACAT inhibitors and bile acid sequestrants as a means of lowering plasma cholesterol and as a means of treating atherosclerosis. Alternatively, the compound of this invention may be used in conjunction with an antifungal agent such as those conventional in the art (e.g., lanosterol demethylase inhibitor) for the treatment of a fungal infection. Alternatively, they may be used in conjunction with another anti-acne agent (e.g. a topical or oral antibiotic both of which are conventional in the pharmaceutical industry). In combination therapy treatment, both the squalene synthetase inhibitors of this invention and the other drug therapies are administered to mammals (e.g., humans) by conventional methods.

In particular, other cholesterol absorption inhibitors and cholesterol synthesis inhibitors are described further below.

Other cholesterol absorption inhibitors are described for example, in PCT WO 94/00480.

Any HMG-CoA reductase inhibitor may be used as the second compound in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP491226A (the disclosure of which is incorporated by reference) discloses certain pyridyldihydroxyheptenoic acids, such as rivastatin. In addition, U.S. Pat No. 4,647,576 (the disclosure of which is incorporated by reference) discloses certain 6-[2-(substituted-pyrrol-1-yl)alkyl]pyran-2-ones such as atorvastatin.

Any HMG-CoA synthase inhibitor may be used as the second compound in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below however other HMG-CoA synthase inhibitors will be known to those skilled in the art. U.S. Pat. No. 5,120,729 (the disclosure of which is hereby incorporated by reference) disclose certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block the transcription of DNA or translation inhibitors that prevent translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol. 1985; 110:9–19). Several compounds are described and referenced below however other inhibitors of HMG-CoA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog.Lip. Res. 1993;32:357–416).

Any squalene epoxidase inhibitor may be used as the second compound in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466–471). A variety of these compounds are described and referenced below however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication 9410150 (the disclosure of which is hereby incorporated by reference) discloses certain 1,2,3,5,6,7,8,8α-octahydro-5,5,8α(beta)-trimethyl-6-isoquinolineamine derivatives, such as N-trifluoroacetyl-1,2,3,5,6,7,8,8α-octahydro-2-allyl-5,5,8α(beta)-trimethyl-6(beta)-isoquinolineamine. French patent publication 2697250 (the disclosure of which is hereby incorporated by reference) discloses certain beta, beta-dimethyl-4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays (certain experimental conditions) it is not possible to distinguish between squalene epoxidase inhibitors and squalene cyclase inhibitors, however, these assays (experimental conditions) are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below however other squalene epoxidase/squalene cyclase inhibitors will be known to those skilled in the art U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl) pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

Any lanosterol demethylase inhibitor may be used as the second compound in the combination aspect of this invention. The term lanosterol demethylase inhibitor refers to compounds which inhibit the 14-demethylation of lanosterol catalyzed by the enzyme lanosterol demethylase. Such inhibition is readily determined by those skilled in the art according to standard assays (Biochemistry 1994; 33:4702–4713 and references cited therein). A variety of these compounds are described and referenced below however other lanosterol demethylase inhibitors will be known to those skilled in the art such as fluconazole and voriconazole. Voriconazole is exemplified in U.S. Pat. No. 5,278,175 (the disclosure of which is hereby incorporated by reference) and is (2R, 3S)-2-(2,4-difluorophenyl)-3-(5-fluoropyrimidin-4-yl)-1-(1,2,4-triazol-1-yl)butan-2-ol. U.S. Pat. Nos. 4,782,059 and 4,894,375 (the disclosures of which are hereby incorporated by reference) disclose certain azoles such as cis-1-acetyl 4-(4-((2-(2,4-dichlorophenyl)-2-(1H-imidazol-1-ylmethyl)1,3-dioxolan-4-yl)methoxy)phenyl) piperazine (ketoconazole). EP publication 492474A (the disclosure of which is hereby incorporated by reference) discloses certain dioxolanes such as (2S,4S)-Cis-2-(2-(4-chlorophenyl)ethyl)-2-imidazol-1-yl)methyl-4-(4-aminophenyl-thio)methyl-1,3-dioxolane. U.S. Patent No. 5,041,432 (the disclosure of which is hereby incorporated by reference) discloses certain 15-substituted lanosterol derivatives.

The compounds of this invention can be administered individually or together in any conventional oral or parenteral dosage form such as a capsule, tablet, powder, cachet, suspension or solution. For oral administration, which is preferred, a pharmaceutical composition can take the form of solutions, suspensions, tablets, pills, capsules, powders, and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound(s) according to the invention as an active ingredient. In addition, it may include other medicinal or pharmaceutical agents, carriers, adjuvants, etc.

Pharmaceutical compositions according to this invention may contain 0.1%–95% of the compound(s) of this invention, preferably 1%–70%. In any event, the composition or formulation to be administered will contain a quantity of a compound(s) according to the invention in an amount effective to treat the condition of the subject being treated, i.e., hypercholesterolemia, atherosclerosis, Alzheimer's disease or fungal infection.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administerable compositions can be prepared by dissolving or dispersing, or otherwise preparing a compound(s) according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent in light of this disclosure, to those skilled in this art. For examples, see Remington's Pharmaceutical Sciences., Mack Publishing Company, Easter, Pa., 15th Edition (1975).

Since the present invention has an aspect that relates to the treatment of hypercholesterolemia, a fungal infection or acne with a combination of active ingredients which may be administered separately, the invention also relates to combining separate pharmaceutical compositions in kit form. The kit comprises two separate pharmaceutical compositions: a compound of Formula I and a second compound as described above. The kit comprises container means for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also a daily dose of Formula I compound can consist of one tablet or capsule while a daily dose of the second compound can consist of several tablets or capsules and vice versa. The memory aid should reflect this.

In another specific embodiment of the invention a dispenser designed to dispense the daily doses one at a time in the order of their intended use is provided.

Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

In the Examples below proton nuclear magnetic resonance spectra ($^1$H NMR) and nuclear magnetic resonance spectra ($C^{13}$ NMR) were measured for solutions in deuterated solvent. Unless otherwise stated, the NMR spectra were recorded on a 300 MHz instrument. The peak shapes are denoted as follows: s, singlet; d, doublet; t, triplet, q, quartet; m, multiplet; br, broad; c, complex.

EXAMPLE 1

N-[trans-7-chloro-5-(1-naphthyl)-1-(3-hydroxy-2,2-dimethyl-propyl)-2-oxo-1,2,3,5-tetrahydro-4,1-benzothiazepin-3-acetyl]isonipecotic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1N sulfuric acid) were added to each of 6 125-mL Delong flasks with Morton closures and the resulting combinations were steam-sterilized for 30 minutes at 15 psig and 121° C. One flask was aseptically inoculated with a loopful of growth taken from an agar slant of an axenic culture of *Streptomyces griseus* (American Type Culture Collection strain 13273) grown on yeast malt extract agar (ATCC Medium 196). This inoculum flask was mounted vertically on a gyratory shaker (2-inch throw) and shaken at 210 rpm and 28° C. for 2 days. Then, each of the 5 additional flasks containing IOWA Medium were aseptically inoculated with 0.25 mL of vegetative culture (cells and growth medium) taken from the inoculum flask. The resulting 5 biotransformation flasks were mounted vertically on the gyratory shaker and shaken at 210 rpm and 28° C. for 2 days. (-)-N-[trans-7-chloro-5-(1-naphthyl)-1-neopentyl-2-oxo-1,2,3,5-tetrahydro4, 1-benzothiazepin-3-acetyl] isonipecotic acid was dissolved in dimethylformamide (20 mg/mL) and sterilized by membrane filtration (0.2 micron porosity). To each of the 5 biotransformation flasks, 0.25 mL of the resulting solution was aseptically added to give an initial substrate concentration of 200 mcg/mL. The dosed flasks were mounted vertically on the gyratory shaker and shaken at 210 rpm and 28° C. for 7 days. The contents of the biotransformation flasks were extracted with chloroform (3×; 150 mL total/flask). The chloroform extraction layers were recovered, combined, dried over anhydrous magnesium sulfate (0.5–1 g), filtered to remove solids, and concentrated to dryness under reduced pressure. The dried crude (85.1 mg) was redissolved in methanol (400 mcL), centrifuged (16,000×g, 5 min.) to remove insolubles, and purified by reversed phase high performance liquid chromatography (HPLC method #1).

HPLC Method #1

Column: Nova-Pak C18, 7.8×300 mm.

Mobile phase: 60% acetonitrile: 40% aqueous buffer (0.05M monopotassium hydrogen phosphate, adjusted to pH 3.5 with phosphoric acid).

Flow rate: isocratic, 5.0 mL/min.

Monitor: UV absorbance at 221 nm; photodiode array at 195–400 nm.

Run Time: 12 min.

The title compound had a retention time of 2.4 minutes and absorbance maxima at 219 nm and 266 nm. HPLC mobile phase fractions (34 mL) containing the title compound were retained and extracted with chloroform (2×; 140 mL total). The chloroform extraction layer was recovered, dried over anhydrous magnesium sulfate, filtered to remove solids, and concentrated to dryness under reduced pressure to produce 2.7 mg of the title compound. The overall process yield was 11%.

MS (FAB): 595 (M+H).

$^1$H-NMR (300 MHz, CDCl$_3$): δ1.02 (m, 6H), 1.52 (m, 2H), 1.86 (m, 2H), 2.30 (m, 1H), 2.50 (m, 1H), 2.77 (t, 1H), 3.09 (m, 2H), 3.26 (m, 1H), 3.43 (m, 2H), 3.74 (m, 1H), 3.84 (m, 1H), 4.20 (m, 2H), 6.37 (s, 1H), 6.68 (d, 1H), 7.20 (m, 1H), 7.29 (m, 1H), 7.35 (d, 1H), 7.39 (m, 1H), 7.48 (t, 1H), 7.75 (d, 1H), 7.82 (d, 2H), 7.85 (d, 1H).

EXAMPLE 2 trans-7-chloro5-(naphthalen-1-yl)-1-(3-hydroxy-2-hydroxymethyl-2-methyl-propyl)-1,2,3,5-tetrahydro-2-oxo-4,1-benzoxazepine-3-acetic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1N sulfuric acid) were added to a 125-mL Delong flask with a Morton closure and the resulting combination was steam-sterilized for 30 minutes at 15 psig and 121° C. The flask was aseptically inoculated with a loopful of growth taken from an agar slant of an axenic culture of Actinoplanes sp. (American Type Culture Collection strain 53771) grown on IOWA Medium agar (IOWA Medium plus 15 g agar). The flask was mounted vertically on a gyratory shaker (2-inch throw) and shaken at 210 rpm and 28° C. for 2 days. Trans-7-chloro-5-(naphthalen-1-yl)-1-neopentyl-1,2,3,5-tetrahydro-2-oxo-4,1-benzoxazepine-3-acetic acid was dissolved in dimethylsulfoxide (20 mg/mL) and sterilized by membrane filtration (0.2 micron porosity). To the biotransformation flask, 0.25 mL of the resulting solution was aseptically added to give an initial substrate concentration of 200 mcg/mL. The dosed flask was mounted vertically on the gyratory shaker and shaken at 210 rpm and 28° C. for 5 days. The contents of the biotransformation flask were extracted with ethyl acetate (3×; 150 mL total/flask). The ethyl acetate extraction layers were recovered, combined, and concentrated to dryness under reduced pressure. The dried crude was redissolved in methanol and purified by reversed phase high performance liquid chromatography (HPLC method #2).

HPLC Method #2

Column: Microsorb C18, 10×250 mm.

Mobile phase: 35% acetonitrile : 35% methanol: 40% aqueous buffer (0.01M monopotassium hydrogen phosphate)

Flow rate: isocratic, 5.0 mL/min.

Monitor UV absorbance at 214 nm; photodiode array at 195–400 nm.

Run Time: 30 min.

The title compound had a retention time of 4.1 minutes and absorbance maxima at 223 nm and 252 nm. HPLC mobile phase fractions containing the title compound were retained and extracted with chloroform. The chloroform extraction layer was recovered, dried over anhydrous sodium sulfate, filtered to remove solids, and concentrated to dryness under reduced pressure to produce 2.0 mg of the title compound. The overall process yield was 40%.

MS (Thermospray): 484 (M+H).

$^1$H-NMR (500 MHz, CDCl$_3$): ppm, 7.94 (d, 2H), 7.85 (d, 1H), 7.65 (d, 1H), 7.59 (t, 1H), 7.48 (t, 1H), 7.38 (t, 1H), 7.30 (m, 2H), 6.66 (s, 1H), 6.50 (d, 1H), 4.75 (d, 1H), 4.48 (t, 1H), 3.75 (t, 1H), 3.65 (m, 2H), 3.10 (dd, 1H), 2.90 (dd, 1H), 2.34 (t, 1H),1.20 (3H).

EXAMPLE 3 trans-7-chloro-5-(naphthalen-1-yl)-1-(3-hydroxy-2,2-dimethyl-propyl)-1,2,3,5-tetrahydro-2-oxo-4,1-benzoxazepine-3-acetic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1N sulfuric acid) were added to each of three 125-mL Delong flasks with Morton closures and the resulting combinations were steam-sterilized for 30 minutes at 15 psig and 121° C. Each of the 3 flasks was aseptically inoculated with 0.25 mL of an axenic suspension of spores of *Absidia pseudocylindrospora* (American Type Culture Collection strain 24169) in Dulbecco's phosphate-buffered saline. The flasks were mounted vertically on a gyratory shaker (2-inch throw) and shaken at 210 rpm and 28° C. for 2 days. Trans-7-chloro-5-(naphthalen-1-yl)-1-neopentyl-1,2,3,5-tetrahydro-2-oxo-4,1-benzoxazepine-3-acetic acid was dissolved in dimethylsulfoxide (20 mg/mL) and sterilized by membrane filtration (0.2 micron porosity). To each of the 3 biotransformation flasks, 0.25 mL of the resulting solution was aseptically added to give an initial substrate concentration of 200 mcg/mL. The dosed flasks were mounted vertically on the gyratory shaker and shaken at 210 rpm and 28° C. for 5 days. The contents of the biotransformation flasks were extracted with ethyl acetate (3×; 150 mL total/flask). The ethyl acetate extraction layers were recovered, combined, and concentrated to dryness under reduced pressure. The dried crude was extracted with hexanes and the resulting deffated crude (30 mg) then was redissolved in methanol, and purified by reversed phase high performance liquid chromatography (HPLC method #3).

HPLC Method #3

Column: Kromasil C4, 10×250 mm.

Mobile phase: 35% acetonitrile : 35% methanol: 40% aqueous buffer (0.01M monopotassium hydrogen phosphate)

Flow rate: isocratic, 5.0 mL/min.

Monitor UV absorbance at 214 nm; photodiode array at 195–400 nm.

Run Time: 30 min.

The title compound had a retention time of 5.5 minutes and absorbance maxima at 223 nm and 252 nm. HPLC mobile phase fractions containing the title compound were retained and extracted with chloroform. The chloroform extraction layer was recovered, dried over anhydrous sodium sulfate, filtered to remove solids, and concentrated to dryness under reduced pressure to produce 2.7 mg of the title compound. The overall process yield was 18%.

MS (Thermospray): 468 (M+H).

$^1$H-NMR (500 MHz, CDCl$_3$): ppm, 8.35 (d,1H), 7.70 (1H), 7.50 (t, 1H), 7.48–7.30 (m, 5H), 6.95 (d, 1H), 6.55 (d, 1H), 4.61 (d, 1H), 4.48 (t 1H), 3.48 (d, 1H), 3.10 (dd, 1H), 2.90 (dd, 1H), 1.30 (s, 3H), 1.10 (s, 3H).

EXAMPLE 4

3-tert-Butyldiphenylsilyloxy-2,2-dimethylpropanal

3-Hydroxy-2,2-dimethylpropanal (5.1 g, 50 mmol) and tert-butyl-diphenylsilyl chloride (15.10 g, 55 mmol) were dissolved in dimethylformamide (50 ml). Imidazole (3.74 g, 55 mmol) was added in one portion. After stirring for 18 hours the mixture was hydrolyzed with water and extracted several times with ether. The combined organic layers were dried with MgSO$_4$. The filtrate was concentrated under reduced pressure, and the residue was purified by flash chromatography (hexane/ethyl acetate 15:1) to give the title compound (9.55 g, 56%) as a colorless oil.

$^1$H NMR (300 MHz, CDCl$_3$): δ9.63 (s, 1H), 7.70 (m, 4H), 7.38 (m, 6H), 3.68 (s, 2H), 1.08 (s, 15H).

EXAMPLE 5

α-(1-Naphthyl)-2-(3-tert-butyldiphenylsilyloxy-2,2-dimethylpropyl)amino-5-chlorobenzyl alcohol Sodium borohydride (1.73 g, 45.8 mmol) was added portionwise to a solution of α-(1-naphthyl)-2-amino-5- chlorobenzyl alcohol (9.76 g, 34.4 mmol) and 3-tert-butyldiphenylsilyloxy-2,2-dimethylpropanal (12.89 g, 37.9 mmol) in acetic acid (105 ml) at 0° C. The reaction mixture was allowed to warm to room temperature, and stirring was continued for 45 min. Hydrolysis with water was followed by repeated extraction of the mixture with ethyl acetate. The combined organic layers were washed with 1 N sodium hydroxide and dried with $MgSO_4$. The filtrate was concentrated under reduced pressure, and the residue was purified by flash chromatography (hexane/ethyl acetate 9:1) to give the title compound (12.01 g, 57%) as a colorless oil.

MS (TSP): 608 (M+H$^+$).

$^1$H NMR (300 MHz, CDCl$_3$): δ7.85 (m, 3H), 7.63 (m, 4H), 7.37 (m, 12H), 7.13 (m, 1H), 6.88 s, 1H), 6.70 (s, 1H), 6.33 (s, 1H), 3.40 (s, 2H), 3.07 (br. s, 2H), 1.07 (s, 9H), 0.87 (s, 6H).

EXAMPLE 6

Ethyl trans-3-{N-[4-chloro-2-(α-hydroxy-1-naphthylmethyl)phenyl]-N-[3-tert-butyldiphenylsilyloxy-2,2-dimethylpropyl]-N-carbamoyl} acrylate α-(1-Naphthyl)-2-(3-tert-butyldiphenylsilyloxy-2,2-dimethylpropyl)amino-5-chlorobenzyl alcohol (12.0 g, 19.7 mmol) and monoethyl fumarate chloride (4.17 g, 25.7 mmol) were dissolved in dichloromethane (300 ml) followed by addition of sodium bicarbonate (3.32 g, 39.5 mmol) at room temperature. The mixture was stirred for 18 h, then hydrolyzed with water and extracted several times with dichloromethane. The combined organic layers were dried with $MgSO_4$. The filtrate was concentrated under reduced pressure to give the title compound as a colorless oil (14.49 g) which was used without further purification.

MS (TSP): 735 (M+H$^+$).

EXAMPLE 7

Ethyl trans-7-chloro-5-(1-naphthyl)-1-(3-tert-butyldiphenylsilyloxy-2,2-dimethylpropyl)-2-oxo-1, 2,3,5-tetrahydro-4,1-benzoxazepine-3-acetate Ethyl trans-3-{N-[4-chloro-2-(α-hydroxy-1-naphthylmethyl)phenyl]-N-[3-tert-butyldiphenylsilyloxy-2, 2-dimethylpropyl]-N-carbamoyl} acrylate (14.49 g) and potassium carbonate (5.45 g, 39.5 mmol) were dissolved in ethanol (150 ml) and stirred for 3 days at room temperature. The solvent was evaporated, and the residue was partitioned between ethyl acetate and water. The aqueous layer was further extracted with ethyl acetate, and the combined organic layers were dried with $MgSO_4$. The filtrate was concentrated under reduced pressure, and the residue was purified by flash chromatography (toluene/ethyl acetate 60:1) to provide the title compound (7.32 g, 50% yield for 2 steps.).

MS (TSP): 735 (M+H$^+$).

$^1$H NMR (300MHz, CDCl$_3$): δ7.89 (d, 2H), 7.79 (d, 1H), 7.57 (m, 3H), 7.27 (m, 13H), 6.52 (m, 2H), 4.52 (m, 2H), 4.15 (q, 2H), 3.89 (d, 1H), 3.40 (dd, 2H), 2.95 (ddd, 2H), 1.23 (t, 3H), 1.09 (s, 12H), 0.99 (s, 3H).

EXAMPLE 8

Ethyl trans-7-chloro-5-(1-naphthyl)-1-(2,2-dimethyl-3-hydroxypropyl)-2-oxo-1,2,3,5-tetrahydro-4,1-benzoxazepine-3-acetate Ethyl trans-7-chloro-5-(1-naphthyl)-1-(3-tert-butyldiphenylsilyloxy-2,2-dimethylpropyl)-2-oxo-1,2,3,5-tetrahydro-4,1-benzoxazepine-3-acetate (8.52 g, 11.62 mmol) was dissolved in acetonitrile (200 ml). A solution of HF in water (50%, 50 ml) was added at room temperature. Stirring for 18 hours was followed by hydrolysis with saturated sodium bicarbonate and repeated extraction of the aqueous layer with dichloromethane. The combined organic layers were dried with $MgSO_4$. The filtrate was concentrated under reduced pressure, and the residue was purified by flash chromatography (dichloromethane/methanol 99:1) to give the title compound (4.64 g, 81%) as a colorless solid.

MS (TSP): 496 (M+H$^+$).

$^1$H NMR (300 MHz, CDCl$_3$): δ7.91 (d, 2H), 7.81 (d, 1H), 7.57 (t, 1 H), 7.38 (m, 5H), 6.55 (s, 1H), 6.52 (s, 1H), 4.54 (m, 2H), 4.15 (q, 2H), 3.87 (m, 1H),3.65 (m, 1H), 3.55 (d, 1 H), 3.24 (t,1 H), 2.97 (ddd, 2H), 1.26 (t, 3H), 1.11 (s, 3H), 0.82 (s, 3H).

EXAMPLE 9

Ethyl trans-7-chloro-5(1-naphthyl)-1-(2-formyl-2-methylpropyl)-2-oxo-1,2,3,5-tetrahydro-4,1-benzoxazepine-3-acetate Dimethyl sulphoxide (1.61 g, 20.6 mmol) was added dropwise to a solution of oxalyl chloride (1.31 g, 10.3 mmol) in dichloromethane (75 ml) at −60° C. The mixture was stirred until gas evolution had ceased. Ethyl trans-7-chloro-5-(1-naphthyl)-1-(2,2-dimethyl-3 -hydroxypropyl)-2-oxo-1, 2,3,5-tetrahydro-4,1-benzoxazepine-3-acetate (4.6 g, 9.4 mmol), dissolved in dichloromethane (30 ml), was added dropwise over a period of 5 min. at −60° C., and stirring was continued for further 15 min. The mixture was quenched with triethylamine (4.73 g, 46.8 mmol) before allowing to warm to room temperature. Addition of water, separation of the organic layer and repeated extraction of the aqueous layer with dichloromethane was followed by drying of the combined organic layers with $MgSO_4$. The filtrate was concentrated under reduced pressure, and the residue was purified by flash chromatography (dichloromethane/methanol 99:1) to give the title compound (4.62 g, 99%).

MS (TSP): 494 (M+H$^+$).

$^1$H NMR (300 MHz, CDCl$_3$): δ9.62 (s, 1H), 7.90 (d, 2H), 7.81 (d, 1H), 7.59 (m, 2H), 7.42 (m, 4H), 6.53 (s, 1H), 6.48 (s, 1H), 4.69 (d, 1H), 4.53 (t, 1H), 4.15 (q, 2H), 3.82 (d, 1H), 2.95 (ddd, 2H), 1.30 (s, 3H), 1.25 (t, 3H), 1.13 (s, 3H).

EXAMPLE 10

Ethyl trans-7-chloro-5-(1-naphthyl)-1-(2,2-dimethyl-3-dimethylamino-propyl)-2-oxo-1,2,3,5-tetrahydro-4,1-benzoxazepine-3-acetate Dimethylamine (0.18 g, 4.0 mmol) was added to ethyl trans-7-chloro-5-(1-naphthyl)-1-(2-formyl-2-methylpropyl)-2-oxo-1,2,3,5-tetrahydro-4,1 -benzoxazepine-3-acetate (2.0 g, 4.05 mmol) in titanium tetraisopropoxide (3.45 g, 12.15 mmol) at room temperature. Stirring for 1h was followed by addition of sodium cyanoborohydride (0.38 g, 6.0 mmol) and ethanol (20 ml). The mixture was stirred for another 18 hours before 2 N sodium hydroxide was added. The mixture was extracted several times with dichloromethane, and the combined organic layers were dried with $MgSO_4$. The filtrate was concentrated under reduced pressure, and the residue was purified by flash chromatography (dichloromethane/methanol/aqueous ammonia 99:1:0.1 to 98:2:0.2) to give the title compound (1.23 g, 58%) as a yellow oil.

MS (TSP): 523 (M+H⁺).

¹H NMR (300 MHz, CDCl₃): δ7.90 (d, 2H), 7.82 (d, 1H), 7.58 (t, 1H), 7.42 (m, 5H), 6.63 (s, 1H), 6.53 (s, 1H), 4.55 (m, 2H), 4.17 (q, 2H), 3.70 (d, 2H), 2.97 (ddd, 2H), 2.28 (s, 6H), 1.26 (t, 3H), 1.10 (s, 3H), 0.95 (s, 3H).

EXAMPLE 11

Ethyl trans-7-chloro-5-(1-naphthyl)-1-(2.2-dimethyl-3-(4-morpholino)-propyl)-2-oxo -1,2,3,5-tetrahydro-4,1-benzoxazepine-3-acetate The title compound was prepared using a method analogous to that described in example 10 except using I equivalent of morpholine and stirring the mixture for 5 hours.

54 % yield.

MS (TSP): 565 (M+H⁺).

¹H NMR (300 MHz, CDCl₃): δ7.92 (d, 2H), 7.83 (t, 1H), 7.58 (t, 1H), 7.39 (m, 5H), 6.59 (d, 1H), 6.52 (s, 1H), 4.55 (m, 2H), 4.17 (q, 2H), 3.85 (m, 1H), 3.65 (s, 3H), 3.23 (t, 1H), 3.10 (m, 1H), 2.97 (ddd, 2H), 2.45 (m, 4H), 1.25 (t, 3H), 1.10 (s, 3H), 0.93 (s, 3H).

EXAMPLE 12

Trans-7-chloro-5-(1 -naphthyl)-1-(2,2-dimethyl-3-dimethylaminopropyl)-2-oxo-1,2,3,5-tetrahydro-4,1-benzoxazepine-3-acetic acid Ethyl trans-7-chloro-5-(1-naphthyl)-1-(2,2-dimethyl-3-dimethylamino-propyl)-2- oxo-1,2,3,5-tetrahydro-4,1-benzoxazepine-3-acetate (212 mg, 0.41 mmol) and potassium carbonate (112 mg, 0.83 mmol) were stirred in a mixture of MeOH (8 ml) and water (2.5 ml) for 18 hours at 60° C. The mixture was cooled to room temperature, acidified to pH 2 with 2N HCl and extracted several times with ethyl acetate. The combined organic layers were dried with MgSO₄. The filtrate was concentrated under reduced pressure to give the title compound (156 mg, 76%).

MS (TSP): 495 (M+H⁺).

¹H NMR (300 MHz, CDCl₃): δ7.90 (d, 2H), 7.82 (d, 1H), 7.70 (d, 1H), 7.58 (t, 1H), 7.42 (m, 3H), 7.32 (m, 2H), 6.53 (s, 1H), 6.45 (s, 1H), 4.63 (d, 1H), 4.19 (d, 1H), 3.33 (d, 1H) 3.08 (s, 6H), 3.03 (m, 1H), 2.97 (ddd, 2H), 1.38 (s, 3H), 1.28 (s, 3H).

EXAMPLE 13

Trans-7-chloro-5-(1-naphthyl)-1-(2,2-dimethyl-3-(4-morpholino)-propyl)-2-oxo-1,2,3,5 -tetrahydro-4,1-benzoxazepine-3-acetic acid The title compound was prepared using a method analogous to that described in example 12 using the compound of Example 11.

99 % yield.

¹H NMR (300 MHz, CDCl₃): δ7.93 (d, 2H), 7.83 (t, 1H), 7.58 (m, 1H), 7.38 (m, 5H), 6.57 (s, 1H), 6.45 (s, 1H), 4.68 (d, 1H), 4.52 (m, 2H), 4.33 (d, 1H), 3.57 (m, 3H) 3.25 (d, 2H), 3.15 (m, 2H), 3.02 (ddd, 2H), 1.12 (s, 3H), 0.87 (s, 3H).

EXAMPLE 14

Trans-7-chloro-5-(1-naphthyl)-1-(2,2-dimethyl-3-dimethylamino-propyl)-2-oxo-1,2,3,5-tetrahydro-4,1-benzoxazepine-3-acetamide Trans-7-chloro-5-(1 -naphthyl)-1 -(2,2-dimethyl-3-dimethylamino-propyl)-2-oxo-1,2,3,5-tetrahydro-4,1-benzoxazepine-3-acetic acid (1.16 g, 2.35 mmol) and 1,1'-carbonyldiimidazole (1.91 g, 11.8 mmol) were dissolved in dimethylformamide (75 ml). Stirring for 1 h at room temperature was followed by addition of ammonium bicarbonate (1.86 g, 23.5 mmol) in one portion to the reaction mixture, which was stirred for further 18 hours at room temperature. The solvent was concentrated under reduced pressure and the residue flash chromatographed directly (dichloromethane/methanol/aqueous ammonia 99:1:0.1 to 98:2:0.2). The solid was taken up in dichloromethane and a stoichiometric amount of 1N HCl in ether was added. Removal of the solvent provided a solid which was dissolved in ethanol and precipitated with ether to give the title compound (0.42 g, 36%) as a colorless solid.

MS (TSP): 494 (M+H⁺).

¹H NMR (300 MHz, DMSO-d₆): δ9.89 (br.. s, 1H), 8.03 (d, 2H), 7.89 (d, 1H), 7.84 (d, 1H), 7.64 (t, 1H), 7.53 (m, 2H), 7.39 (m, 2H), 6.76 (br.. s, 1H), 6.42 (s, 1H), 6.28 (s, 1H), 4.46 (m, 2H), 4.02 (d, 1H), 3.17 (m), 2.85 (br.. s, 6H), 2.65 (ddd, 2H), 1.15 (s, 3H), 1.10 (s, 3H).

EXAMPLE 15

Trans-7-chloro-5-(l-naphthyl)-1-(2,2-dimethyl-3-(4-morpholino)-propyl)-2-oxo-1,2,3,5-tetrahydro-4,1-benzoxazepine-3-acetamide The title compound was prepared using a method analogous to that described in Example 14 using the compound of Example 13.

12% yield.

MS (TSP): 536 (M+H⁺).

¹H NMR (300 MHz, CDCl₃): δ7.92 (d, 1H), 7.85 (d, 2H), 7.60 (t,1H), 7.43 (m, 5H), 6.62 (s, 1H), 6.53 (s, 1H), 5.77 (br.. s, 1H), 5.33 (br.. s, 1H), 4.55 (m, 2H), 3.67 (m, 5H), 2.85 (ddd, 2H), 2.47 (m, 4H), 1.10 (s, 3H), 0.97 (s, 3H).

EXAMPLE 16

Ethyl trans-3-{N-[4-chloro-2-(1-naphthoyl)phenyl]-N-carbamoly} acrylate

Monoethyl fumarate chloride (6.1 g, 37 mmol) was added dropwise to a suspension of sodium bicarbonate (5.0 g, 59 mmol) and 2-amino-5-chlorophenyl-(1-naphthyl) ketone (10.0 g, 35 mmol) in dichloromethane (200 ml). The solution was stirred at room temperature for 18 hours and was then washed with water (100 ml), dried (MgSO₄) and evaporated under reduced pressure to yield a yellow oil. The oil dissolved in ether (50 ml) then deposited the title compound (13.3 g, 92%) as a colorless solid.

¹H NMR (300 MHz, CDCl₃): δ11.85 (br.s, 1H), 8.87 (d, 1H), 8.06 (dd, 1H), 7.96 (dd, 2H), 7.5–7.6 (m, 5H), 7.44 (d, 1H), 7.14 (d, 1H), 6.97 (d, 1H), 4.28 (q, 2H), 1.34 (t, 3H).

EXAMPLE 17

Ethyl trans-3-{N-[4-chloro-2-(1-naphthoyl)phenyl]-N-[4-iodobutyl]-N-carbamoyl} acrylate Sodium hydride (60%, 981 mg, 24.5 mmol) was added portionwise to a solution of ethyl trans-3-{N-[4-chloro-2-(1-naphthoyl)phenyl]-N-carbamoyl} acrylate (10.0 g, 24.5 mmol) in DMF (100 ml) at ice bath temperature under a nitrogen atmosphere. The resulting mixture was stirred at this temperature for 1 hour, following which 1,4-diiodobutane (8.1 ml, 61.25 mmol) was added in one aliquot. The resulting solution was stirred at 25° C. for 18 hours. The solvent was removed under reduced pressure and the resulting residue dissolved in diethyl ether and washed with water (4×). The organic layer was dried (MgSO₄), concentrated under reduced pressure and purified by flash column chromatography (ethyl acetate/hexane 1:9→1:4) to give the title compound (8.09, 55%) as a pale yellow oil.

MS (TSP): 590 (M+H⁺).

$^1$H NMR (300 MHz, CDCl$_3$) δ8.58 (d, 1H), 8.02 (d, 1H), 7.90 (d, 1H), 7.64–7.53 (m, 5H), 7.40 (t, 1H), 7.21 (d, 1H), 6.75 (d, J=15.4 Hz, 1H), 6.66 (d, J=15.4 Hz, 1H), 4.19 (q, 2H), 4.04 (m, 1H), 3.99–3.07 (m, 3H), 1.76 (m, 2H), 1.64 (m, 2H), 1.28 (t, 3H).

EXAMPLE 18

Ethyl trans-7-chloro-5-(1-naphthyl)-1-(4-iodobutyl)-2-oxo-1,2,3,5-tetrahydro-4,1-benzoxazepine-3-acetate Sodium borohydride (385 mg, 10.2 mmol) was added portionwise to a solution of ethyl trans-3-{N-[4-chloro-2-(1-naphthoyl)phenyl]-N-[4-iodobutyl]-N-carbamoyl} acrylate (8.0 g, 13.6 mmol) in methanol (100 ml) at 25° C. The resulting mixture was stirred for 1.5 hours. The mixture was acidified with 2N hydrochloric acid and concentrated under reduced pressure. The residue was dissolved in ethyl acetate and washed with water (2×). The organic layer was dried (MgSO$_4$), and evaporated under reduced pressure to give a pale yellow oil.

Potassium carbonate (937 mg, 6.8 mmol) was added to a solution of the above oil in ethanol (100 ml) at 25° C. The resulting mixture was stirred at room temperature for 72 hours. The solvent was removed under reduced pressure and the resulting residue dissolved in ethyl acetate and washed with water (3×50 ml). The organic layer was dried (MgSO$_4$), and evaporated under reduced pressure to give a yellow oil. The oil dissolved in ethanol then deposited the title compound (5.09 g, 63%) as a colorless solid.

MS (TSP): 592 (M+H⁺)

$^1$H NMR (400 MHz, CDCl$_3$) δ7.93–7.84 (m, 3H), 7.60 (t, 1H), 7.47–7.32 (m, 5H), 6.54 (d, 1H), 6.42 (s, 1H), 4.53 (m, 2H), 4.17 (q, 2H), 3.74 (m, 1H), 3.29 (t, 2H), 3.10 (dd, J=8.3 Hz, 1H), 2.87 (dd, J=10.5 Hz, 1H), 1.97 (m, 4H), 1.27 (t, 3H).

EXAMPLE 19

Trans-7-chloro-5-(1-naphthyl)-1-(4-iodobutyl)-2-oxo-1,2,3,5-tetrahydro-4,1-benzoxazepine-3-acetonitrile Trimethylaluminium (2M in toluene, 15.0 ml, 30.1 mmol) was added dropwise to a suspension of ammonium chloride (1.6 g, 30.1 mmol) in toluene (25 ml) at ice bath temperature under a nitrogen atmosphere. The resulting solution was stirred for 1 hour. Ethyl trans-7-chloro-5-(1-naphthyl)-1-(4-iodobutyl)-2-oxo-1,2,3,5-tetrahydro-4,1-benzoxazepine-3-acetate (5.1 g, 8.6 mmol) was added as a solid and the solution heated at 85° C. for 18 hours. The solution was cooled and acidified with 2 N hydrochloric acid cautiously. Ethyl acetate (100 ml) was added and the layers were separated. The organic layer was washed with 2 N hydrochloric acid. The combined acidic layers were re-extracted once with ethyl acetate. The combined organic layers were washed with 1N sodium hydroxide solution (2×), dried (MgSO$_4$), concentrated under reduced pressure. The residue was purified by flash column chromatography (ethyl acetate/hexane 1:4→2:3) to give a solid which was recrystallized from ethyl acetate/hexane to afford the title compound (1.58 g, 34%) as a pink solid.

M.p.=174–176° C.

MS (TSP): 562 (M+NH$_4$⁺)

$^1$H NMR (400 MHz, CDCl$_3$) δ7.96–7.92 (m, 3H), 7.64 (t, 1H), 7.50–7.38 (m, 3H), 7.35 (d, 1H), 7.23 (d, 1H), 6.57 (d, 1H), 6.47 (s, 1H), 4.53 (m, 1H), 4.36 (dd, J=6+8hz, 1H), 3.73 (m, 1H), 3.29 (m, 2H), 3.00 (dd, J=7.6+16.8 Hz, 1H), 2.92 (dd, J=5.6+16.8 Hz, 1H), 2.02–1.90 (m, 4H).

EXAMPLE 20

Trans-7-chloro-5-(1-naphthyl)-1-(4-(2-methylimidazol-1-yl) butyl)-2-oxo-1,2,3,5-tetrahydro-4,1-benzoxazepine-3-acetonitrile Trans-7-chloro-5-(1-naphthyl)-1-(4-iodobutyl)-2-oxo-1,2,3,5-tetrahydro-4,1-benzoxazepine-3-acetonitrile (575 mg, 1.06 mmol), 2-methylimidazole (87 mg, 1.06 mmol) and potassium carbonate (146 mg, 1.06 mmol) were dissolved in DMF (5 ml) and the resulting solution stirred at 25° C. for 72 hours. Ethyl acetate was added and the solution washed with water (4×). The organic layer was dried (MgSO$_4$), concentrated under reduced pressure and purified by flash column chromatography (ethyl acetate/diethylamine 95:5) to give the title compound (250 mg, 47%) as a colorless foam.

MS (PCI): 499 (M+H⁺)

$^1$H NMR (300 MHz, CDCl$_3$) δ7.98–7.90 (m, 3H), 7.63 (t, 1H), 7.50–7.43 (m, 2H), 7.34–7.31 (m, 3H), 7.10 (s, 2H), 6.57 (d, 1H), 6.37 (s, 1H), 4.39–4.35 (m, 2H), 4.17 (m, 2H), 3.95 (m, 1H), 2.95 (d, J=6.2 Hz, 2H), 2.82 (s, 3H), 2.00 (m, 4H).

EXAMPLE 21

Trans-7-chloro-5-(1-naphthyl)-1-(4-(2-methylimidazol-1-yl)butyl)-2-oxo-1,2,3,5-tetrahydro-4,1-benzoxazepine-3-acetamide Hydrogen peroxide solution (30% $^w/_v$ in H$_2$O, 4 ml) was added to a suspension of trans-7-chloro-5-(1-naphthyl)-1-(4-(2-methylimidazol-1-yl)butyl)-2-oxo-1,2,3,5-tetrahydro-4,1-benzoxazepine-3-acetonitrile (250 mg, 0.5 mmol) and potassium carbonate (69 mg, 0.5 mmol) in ethanol (10 ml). The mixture was heated at 60° C. for 18 hours. The solvent was removed under reduced pressure, the resulting residue dissolved in dichloromethane and washed with brine. The organic layer was dried (MgSO$_4$), and concentrated under reduced pressure. The residue was purified by flash column chromatography (dichloromethane/methanol/ammonia solution 97:3:1) to give a colorless oil. The oil was triturated with hot ethyl acetate/diethyl ether/hexane to give the title compound (98 mg, 38%) as a colorless solid.

M.p. =222° C.

MS (TSP): 517 (M+H⁺)

$^1$H NMR (400 MHz, CDCl$_3$) δ7.93–7.91 (d, 2H), 7.85 (d, 1H), 7.60 (t, 1H), 7.47 (t, 1H), 7.39 (dd, 1H), 7.34–7.24 (m, 2H), 7.19 (d, 1H), 7.09 (s, 2H), 6.54 (d, 1H), 6.30 (s, 1H), 5.79 (br.s, 1H), 5.70 (br.s, 1H), 4.56 (dd, J=4.6+8.0 Hz, 1H), 4.18–4.10 (m, 4H), 3.03 (dd, J=8.5+15.4 Hz, 1H), 2.84 (s, 3H), 2.75 (dd, J=5.1+15.4 Hz, 1H), 2.05 (m, 4H).

It should be understood that the invention is not limited to the particular embodiments shown and described herein, but that various changes and modifications may be made without departing from the spirit and scope of this novel concept as defined by the following claims.

We claim:
1. A compound of Formula I

FORMULA I

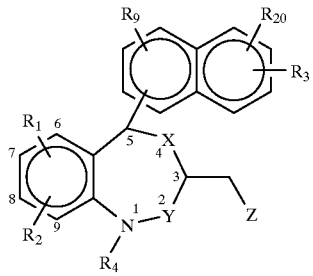

or the pharmaceutically acceptable cationic and anionic salts and stereoisomers thereof wherein X is oxy, thio, —S(O)— or —S(O)$_2$—;

Y is carbonyl or methylene;

$R_1$, $R_2$, $R_3$, $R_{20}$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$)alkoxy, fluorinated ($C_1$–$C_4$)alkoxy having from 1 to 9 fluorines, ($C_1$–$C_4$)alkylthio, ($C_1$–$C_4$) alkylsulfinyl, ($C_1$–$C_4$)alkylsulfonyl, phenyl, amino, mono-N- or di-N,N-($C_1$–$C_4$)alkylamino, carboxyl, ($C_1$–$C_4$)alkoxycarbonyl, carbamoyl, mono-N- or di-N, N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–$C_6$) alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkyl, ($C_1$–$C_7$)alkenyl or ($C_3$–$C_4$) cycloalkylmethyl wherein said ($C_1$–$C_7$)alkyl, ($C_1$–$C_7$) alkenyl or ($C_3$–$C_4$)cycloalkylmethyl are mono-, di-, or tri-substituted wherein the substituents are independently chosen from hydroxyl, oxo, ($C_1$–$C_4$)alkyl, thiol, ($C_1$–$C_4$)alkoxy, fluorinated ($C_1$–$C_4$)alkoxy having from 1 to 9 fluorines, ($C_1$–$C_4$)alkylthio, ($C_1$–$C_4$) alkylsulfinyl, ($C_1$–$C_4$)alkylsulfonyl, or mono-N- or di-N,N($C_1$–$C_4$)alkylaminosulfonyl; or $R_4$ is ($C_1$–$C_7$)alkyl substituted with 4 to 15 fluorines or ($C_3$–$C_4$)cycloalkylmethyl substituted with 1 to 9 fluorines; or $R_4$ is het($C_1$–$C_6$)alkyl wherein het is a 4–7 member saturated or unsaturated heterocycle containing independently one to three O, N or S atoms and said het is optionally mono-substituted with ($C_1$–$C_4$)alkyl, ($C_1$–$C_4$)alkoxy, hydroxyl, halo, amino or mono-N- or di-N,N-($C_1$–$C_4$)alkylamino;

Z is carboxyl, ($C_1$–$C_4$)alkoxycarbonyl, mono-N- or di-N, N-($C_1$–$C_4$)alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ ($C_1$–$C_4$)alkyl, N(R$_{12}$)COR$_{15}$,

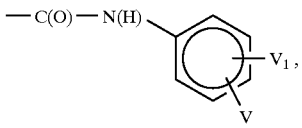

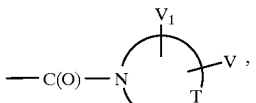

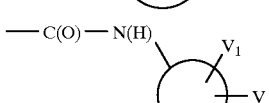

—C(O)—N(H)—W—V or

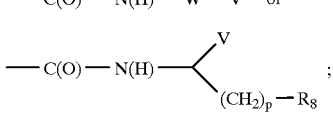

$R_{12}$, $R_{13}$ and $R_{14}$ are each independently H or ($C_1$–$C_4$) alkyl;

$R_{15}$ is H or ($C_1$–$C_4$)alkyl;

$R_5$ is amino or mono-N- or di-N,N-($C_1$–$C_4$)alkylamino; or $R_5$ is ($C_1$–$C_4$)alkyl optionally substituted with 1 to 9 fluorines, amino, mono-N- or di-N,N-($C_1$–$C_4$) alkylamino, carboxyl, ($C_1$–$C_4$)alkoxycarbonyl, carbamoyl or mono-N- or di-N,N-($C_1$–$C_4$) alkylcarbamoyl; phenyl optionally mono- or di-substituted independently with methyl, methoxyl, fluoro, trifluoromethoxyl, carboxyl, ($C_1$–$C_4$) alkoxycarbonyl, methylthio, methylsulfinyl, methylsulfonyl, ($C_1$–$C_4$)alkylsulfonylamino or mono-N- or di-N,N-($C_1$–$C_4$)alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO$_2$R$_7$, hydroxyl or ($C_1$–$C_4$)alkoxy;

$R_7$ is hydrogen or ($C_1$–$C_4$)alkyl;

p is 1, 2, 3 or 4;

$R_8$ is hydroxyl, thiol, carboxyl, ($C_1$–$C_4$)alkoxycarbonyl, carbamoyl, amino, sulfamoyl, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfonyl, ($C_1$–$C_4$) alkylsulfinyl, mono-N- or di-N,N-($C_1$–$C_4$) alkylcarbamoyl, mono-N- or di-N,N-($C_1$–$C_4$) alkylamino, ($C_1$–$C_4$)alkylsulfonylamino, fluorinated ($C_1$–$C_4$)alkylsulfonylamino having from 1 to 9 fluorines, ($C_1$–$C_4$)alkanoylamino, fluorinated ($C_1$–$C_4$) alkanoylamino having from 1 to 9 fluorines, mono-N- or di-N,N-($C_1$–$C_4$)alkylaminosulfonyl, ureido, mono-N- or di-N,N-($C_1$–$C_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be $(C_1-C_7)$alkyl and with the proviso that het cannot have only one heteroatom if that heteroatom is N.

2. A compound of Formula I

FORMULA I

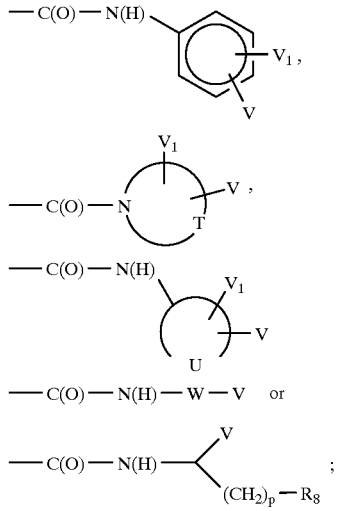

or the pharmaceutically acceptable cationic and anionic salts and stereoisomers thereof
wherein X is oxy, thio, —S(O)— or —S(O)$_2$—;
Y is methylene;
$R_1$, $R_2$, $R_3$, $R_{20}$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N, N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$ alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;
$R_4$ is $(C_1-C_7)$alkenyl or $R_4$ is $(C_1-C_7)$alkyl, $(C_1-C_7)$alkenyl or $(C_3-C_4)$cycloalkylmethyl wherein said $(C_1-C_7)$alkyl, $(C_1-C_7)$alkenyl or $(C_3-C_4)$ cycloalkylmethyl are mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$ alkylsulfinyl, $(C_1-C_4)$alkylsulfonyl, mono-N- or di-N, N-$(C_1-C_4)$alkylamino, mono-N- or di-N,N-$(C_1-C_4)$ alkylaminocarbonyl, or mono-N- or di-N,N$(C_1-C_4)$ alkylaminosulfonyl; or
$R_4$ is $(C_1-C_7)$alkyl substituted with 1 to 15 fluorines or $(C_3-C_4)$cycloalkylmethyl substituted with 1 to 9 fluorines; or
$R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;
Z is carboxyl, $(C_1-C_4)$alkoxycarbonyl, mono-N- or di-N, N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ $(C_1-C_4)$alkyl, N(R$_{12}$)COR$_{15}$, —C(O)—N(H)—⟨ring with V$_1$, V⟩, —C(O)—N⟨ring with V$_1$, V, T⟩, —C(O)—N(H)—⟨ring with V$_1$, V, U⟩

—C(O)—N(H)—W—V or

—C(O)—N(H)—CH(V)(CH$_2$)$_p$—R$_8$ ;

$R_{12}$, $R_{13}$ and $R_{14}$ are each independently H or $(C_1-C_4)$ alkyl;
$R_{15}$ is H or $(C_1-C_4)$alkyl;
$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$ alkylamino, carboxyl, $(C_1-C_4)$alkoxycarbonyl, carbamoyl or mono-N- or di-N,N-$(C_1-C_4)$ alkylcarbamoyl; phenyl optionally mono- or di-substituted independently with methyl, methoxyl, fluoro, trifluoromethoxyl, carboxyl, $(C_1-C_4)$ alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;
T forms a four to seven membered mono-aza, saturated ring, said ring optionally containing thio and said ring optionally mono-substituted on carbon with hydroxyl;
U forms a three to seven membered saturated carbocyclic ring;
V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;
$V_1$ is H, —CO$_2$R$_7$, hydroxyl or $(C_1-C_4)$alkoxy;
$R_7$ is hydrogen or $(C_1-C_4)$alkyl;
p is 1, 2, 3 or 4;
$R_8$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$ alkylsulfinyl, mono-N- or di-N,N-$(C_1-C_4)$ alkylcarbamoyl, mono-N- or di-N,N-$(C_1-C_4)$ alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$ alkanoylamino having from 1 to 9 fluorines, mono-N- or di-N,N-(C₁–C₄)alkylaminosulfonyl, ureido, mono-N- or di-N,N-(C₁–C₄)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that R₄ cannot be (C₁–C₇)alkyl.

3. A compound as recited in claim 1 wherein
the C³ and C⁵ substituents are trans;
R₁ and R₂ are each independently hydrogen, halo, (C₁–C₄)alkyl, (C₁–C₄)alkoxy, hydroxy, trifluoromethyl, (C₁–C₄)alkylthio, fluorinated (C₁–C₄) alkoxy having from 1 to 9 fluorines, (C₁–C₄)alkanoyl or R₁ and R₂ taken together form an ethylenedioxy ring;
R₃, R₂₀ and R₉ are H;
X is oxy;
Y is carbonyl;
V is —CO₂R₇;
V₁ is H; and
Z is carboxyl, tetrazol-5-yl,

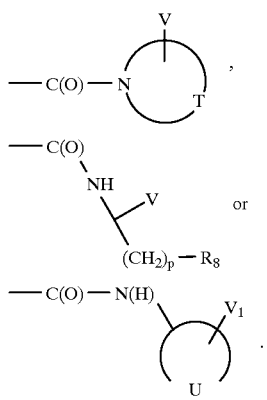

4. A compound as recited in claim 3 wherein
the C⁵ substituent is 1-naphthyl;
T forms a piperidin-1-yl ring; and
R₈ is carboxyl or alkylthio.

5. A compound as recited in claim 4 wherein
R₄ is 2,2-dimethyl-3-hydroxypropyl;
R₁ is 7-chloro;
R₂ is H; and
Z is carboxyl.

6. A compound as recited in claim 3 wherein
R₄ is 2,2-di-(hydroxymethyl)propyl;
R₁ is 7-chloro;
R₂ is H; and
Z is carboxyl.

7. A compound as recited in claim 1 wherein
the C³ and C⁵ substituents are trans;
R₁ and R₂ are each independently hydrogen, halo, (C₁–C₄)alkyl, (C₁–C₄)alkoxy, hydroxy, trifluoromethyl, (C₁–C₄)alkylthio, fluorinated (C₁–C₄) alkoxy having from 1 to 9 fluorines, (C₁–C₄)alkanoyl or R₁ and R₂ taken together form an ethylenedioxy ring;
R₃, R₂₀ and R₉ are H;
X is oxy;
Y is methylene;

V is —CO₂R₇;
V₁ is H; and
Z is carboxyl, tetrazol-5-yl,

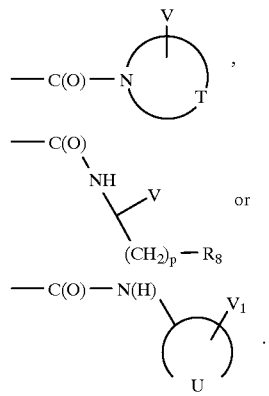

8. A compound as recited in claim 7 wherein
the C⁵ substituent is 1-naphthyl;
Z is

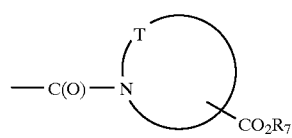

and T forms a piperidin-1-yl ring.

9. A compound as recited in claim 1 wherein
the C³ and C⁵ substituents are trans;
R₁ and R₂ are each independently hydrogen, halo, (C₁–C₄)alkyl, (C₁–C₄)alkoxy, hydroxy, trifluoromethyl, (C₁–C₄)alkylthio, fluorinated (C₁–C₄) alkoxy having from 1 to 9 fluorines, (C₁–C₄)alkanoyl or R₁ and R₂ taken together form an ethylenedioxy ring;
R₃, R₂₀ and R₉ are H;
X is thio;
Y is carbonyl;
V is —CO₂R₇ or tetrazol-5-yl;
V₁ is H; and
Z is carboxyl, tetrazol-5-yl,

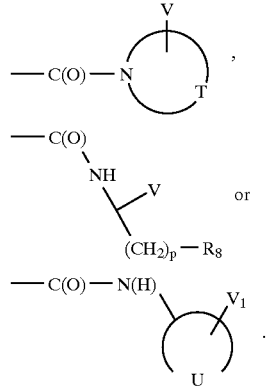

10. A compound as recited in claim 9 wherein
the C⁵ substituent is 1-naphthyl; and T forms a piperidin-1-yl ring.

11. A compound as recited in claim 10 wherein $R_4$ is 2,2-dimethyl-3-hydroxypropyl;

$R_1$ is 7-chloro;

$R_2$ is H; and

Z is 4-carboxylpiperidin-1-yl-carbonyl.

12. The compound as recited in claim 11 wherein the $C^3$ and $C^5$ carbons are each of the (R) configuration.

13. A compound as recited in claim 1 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are each independently halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl, phenyl, amino, mono-N- or di-N,N-$(C_1-C_4)$alkylamino, carboxyl, $(C_1-C_4)$alkoxycarbonyl;

X is oxy or thio;

Y is carbonyl or methylene;

V is —$CO_2R_7$ or tetrazol-5-yl;

$V_1$ is H; and

Z is carboxyl, tetrazol-5-yl,

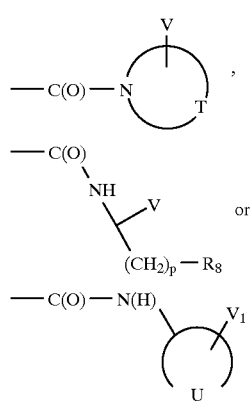

14. A compound as recited in claim 1 wherein
Z is

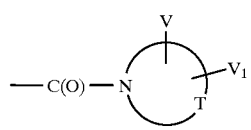

15. A compound as recited in claim 14 wherein the $C^3$ and $C_5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is oxy; and

Y is carbonyl.

16. A compound as recited in claim 15 wherein the $C^5$ substituent is 1-naphthyl; and T forms a piperidin-1-yl ring.

17. A compound as recited in claim 14 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is oxy; and

Y is methylene.

18. A compound as recited in claim 17 wherein the $C^5$ substituent is 1-naphthyl; and T forms a piperidin-1-yl ring.

19. A compound as recited in claim 14 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are H;

X is thio; and

Y is carbonyl.

20. A compound as recited in claim 19 wherein the $C^5$ substituent is 1-naphthyl; and T forms a piperidin-1-yl ring.

21. A compound as recited in claim 14 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_{20}$ and $R_9$ are each independently halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl, phenyl, amino, mono-N- or di-N,N-$(C_1-C_4)$alkylamino, carboxyl, $(C_1-C_4)$alkoxycarbonyl;

X is oxy or thio; and

Y is carbonyl or methylene.

22. A method of treating hypercholesterolemia which comprises administering to a mammal in need of such treatment a hypercholesterolemic treating amount of a compound of Formula I or the pharmaceutically acceptable cationic and anionic salts and stereoisomers of thereof

FORMULA I

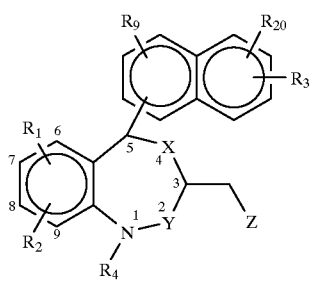

wherein X is oxy, thio, —S(O)— or —S(O)₂—;

Y is carbonyl or methylene;

$R_1$, $R_2$, $R_3$, $R_{20}$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$)alkoxy, fluorinated ($C_1$–$C_4$)alkoxy having from 1 to 9 fluorines, ($C_1$–$C_4$)alkylthio, ($C_1$–$C_4$) alkylsulfinyl, ($C_1$–$C_4$)alkylsulfonyl, phenyl, amino, mono-N- or di-N,N-($C_1$–$C_4$)alkylamino, carboxyl, ($C_1$–$C_4$)alkoxycarbonyl, carbamoyl, mono-N- or di-N, N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–$C_6$) alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkenyl or $R_4$ is ($C_1$–$C_7$)alkyl, ($C_1$–$C_7$) alkenyl or ($C_3$–$C_4$)cycloalkylmethyl wherein said ($C_1$–$C_7$)alkyl, ($C_1$–$C_7$)alkenyl or ($C_3$–$C_4$) cycloalkylmethyl are mono-, di-, or tri-substituted wherein the substituents are independently chosen from hydroxyl, oxo, ($C_1$–$C_4$)alkyl, amino, carboxy, thiol, ($C_1$–$C_4$)alkoxy, fluorinated ($C_1$–$C_4$)alkoxy having from 1 to 9 fluorines, ($C_1$–$C_4$)alkylthio, ($C_1$–$C_4$) alkylsulfinyl, ($C_1$–$C_4$)alkylsulfonyl, mono-N- or di-N, N-($C_1$–$C_4$)alkylamino, mono-N- or di-N,N-($C_1$–$C_4$) alkylaminocarbonyl, or mono-N- or di-N,N($C_1$–$C_4$) alkylaminosulfonyl; or $R_4$ is ($C_1$–$C_7$)alkyl substituted with 1 to 15 fluorines or ($C_3$–$C_4$)cycloalkylmethyl substituted with 1 to 9 fluorines; or $R_4$ is het($C_1$–$C_6$)alkyl wherein het is a 4–7 member saturated or unsaturated heterocycle containing independently one to three O, N or S atoms and said het is optionally mono-substituted with ($C_1$–$C_4$)alkyl, ($C_1$–$C_4$)alkoxy, hydroxyl, halo, amino or mono-N- or di-N,N-($C_1$–$C_4$)alkylamino;

Z is carboxyl, ($C_1$–$C_4$)alkoxycarbonyl, mono-N- or di-N, N-($C_1$–$C_4$)alkylaminocarbonyl, aminocarbonyl, cyano, hydroxyaminocarbonyl, —C(O)N(H)SO₂$R_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N($R_{12}$)CONR$_{13}$R$_{14}$, N($R_{12}$)CO₂ ($C_1$–$C_4$)alkyl, N($R_{12}$)COR$_{15}$,

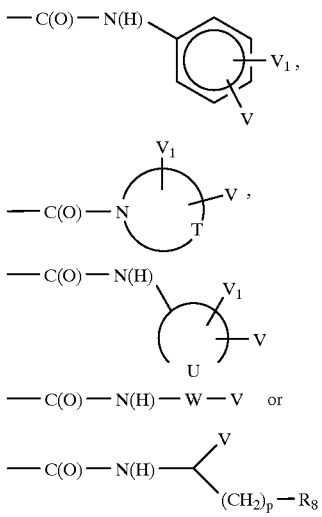

$R_{12}$, $R_{13}$ and $R_{14}$ are each independently H or ($C_1$–$C_4$) alkyl;

$R_{15}$ is H or ($C_1$–$C_4$)alkyl;

$R_5$ is amino or mono-N- or di-N,N-($C_1$–$C_4$)alkylamino; or $R_5$ is ($C_1$–$C_4$)alkyl optionally substituted with 1 to 9 fluorines, amino, mono-N- or di-N,N-($C_1$–$C_4$) alkylamino, carboxyl, ($C_1$–$C_4$)alkoxycarbonyl, carbamoyl or mono-N- or di-N,N-($C_1$–$C_4$) alkylcarbamoyl; phenyl optionally mono- or di-substituted independently with methyl, methoxyl, fluoro, trifluoromethoxyl, carboxyl, ($C_1$–$C_4$) alkoxycarbonyl, methylthio, methylsulfinyl, methylsulfonyl, ($C_1$–$C_4$)alkylsulfonylamino or mono-N- or di-N,N-($C_1$–$C_4$)alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO₂$R_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO₂$R_7$, hydroxyl or ($C_1$–$C_4$)alkoxy;

$R_7$ is hydrogen or ($C_1$–$C_4$)alkyl;

p is 1, 2, 3 or 4;

$R_8$ is hydroxyl, thiol, carboxyl, ($C_1$–$C_4$)alkoxycarbonyl, carbamoyl, amino, sulfamoyl, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfonyl, ($C_1$–$C_4$) alkylsulfinyl, mono-N- or di-N,N-($C_1$–$C_4$) alkylcarbamoyl, mono-N- or di-N,N-($C_1$–$C_4$) alkylamino, ($C_1$–$C_4$)alkylsulfonylamino, fluorinated ($C_1$–$C_4$)alkylsulfonylamino having from 1 to 9 fluorines, ($C_1$–$C_4$)alkanoylamino, fluorinated ($C_1$–$C_4$) alkanoylamino having from 1 to 9 fluorines, mono-N- or di-N,N-($C_1$–$C_4$)alkylaminosulfonyl, ureido, mono-N- or di-N,N-($C_1$–$C_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be ($C_1$–$C_7$)alkyl.

23. A method of treating hypertriglyceridemia which comprises administering to a mammal in need of such treatment a hypertriglyceridemic treating amount of a compound of Formula I or the pharmaceutically acceptable cationic and anionic salts and stereoisomers thereof

FORMULA I

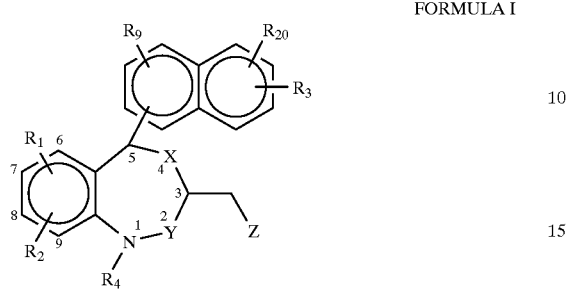

wherein X is oxy, thio, —S(O)— or —S(O)$_2$—;

Y is carbonyl or methylene;

$R_1$, $R_2$, $R_3$, $R_{20}$ and $R_9$ are each independently hydrogen, halo, hydroxyl, trifluoromethyl, (C$_1$–C$_4$)alkyl, fluorinated C$_1$–C$_4$)alkyl having from 1 to 9 fluorines, (C$_1$–C$_4$)alkoxy, fluorinated (C$_1$–C$_4$)alkoxy having from 1 to 9 fluorines, (C$_1$–C$_4$)alkylthio, (C$_1$–C$_4$) alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$)alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_6$)alkanoyl, (C$_1$–C$_6$)alkanoyl(C$_1$–C$_6$)alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is (C$_1$–C$_7$)alkenyl or $R_4$ is (C$_1$–C$_7$)alkyl, (C$_1$–C$_7$) alkenyl or (C$_3$–C$_4$)cycloalkylmethyl wherein said (C$_1$–C$_7$)alkyl, (C$_1$–C$_7$)alkenyl or (C$_3$–C$_4$) cycloalkylmethyl are mono-, di-, or tri-substituted wherein the substituents are independently chosen from hydroxyl, oxo, (C$_1$–C$_4$)alkyl, amino, carboxy, thiol, (C$_1$–C$_4$)alkoxy, fluorinated (C$_1$–C$_4$ )alkoxy having from 1 to 9 fluorines, (C$_1$–C$_4$)alkylthio, (C$_1$–C$_4$) alkylsulfinyl, (C$_1$–C$_4$)alkylsulfonyl, mono-N- or di-N,N-(C$_1$–C$_4$)alkylamino, mono-N- or di-N,N-(C$_1$–C$_4$) alkylaminocarbonyl, or mono-N- or di-N,N(C$_1$–C$_4$) alkylaminosulfonyl; or $R_4$ is (C$_1$–C$_7$)alkyl substituted with 1 to 15 fluorines or (C$_3$–C$_4$)cycloalkylmethyl substituted with 1 to 9 fluorines; or $R_4$ is het(C$_1$–C$_6$)alkyl wherein het is a 4–7 member saturated or unsaturated heterocycle containing independently one to three O, N or S atoms and said het is optionally mono-substituted with (C$_1$–C$_4$)alkyl, (C$_1$–C$_4$)alkoxy, hydroxyl, halo, amino or mono-N- or di-N,N-(C$_1$–C$_4$)alkylamino;

Z is carboxyl, (C$_1$–C$_4$)alkoxycarbonyl, mono-N- or di-N, N-(C$_1$–C$_4$)alkylaminocarbonyl, aminocarbonyl, cyano, hydroxyaminocarbonyl, -C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ (C$_1$–C$_4$)alkyl, N(R$_{12}$)COR$_{15}$,

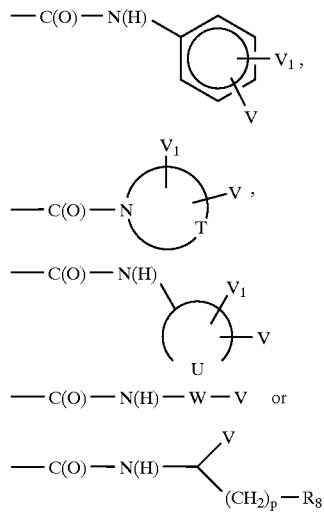

$R_{12}$, $R_{13}$ and $R_{14}$ are each independently H or (C$_1$–C$_4$) alkyl;

$R_{15}$ is H or (C$_1$–C$_4$)alkyl;

$R_5$ is amino or mono-N- or di-N,N-(C$_1$–C$_4$)alkylamino; or $R_5$ is (C$_1$–C$_4$)alkyl optionally substituted with 1 to 9 fluorines, amino, mono-N- or di-N,N-(C$_1$–C$_4$) alkylamino, carboxyl, (C$_1$–C$_4$)alkoxycarbonyl, carbamoyl or mono-N- or di-N,N-(C$_1$–C$_4$) alkylcarbamoyl; phenyl optionally mono- or di-substituted independently with methyl, methoxyl, fluoro, trifluoromethoxyl, carboxyl, (C$_1$–C$_4$) alkoxycarbonyl, methylthio, methylsulfinyl, methylsulfonyl, (C$_1$–C$_4$)alkylsulfonylamino or mono-N- or di-N,N-(C$_1$–C$_4$)alkylaminosulfonyl; or $R_1$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO$_2$R$_7$, hydroxyl or (C$_1$–C$_4$)alkoxy;

$R_7$ is hydrogen or (C$_1$–C$_4$)alkyl;

p is 1, 2, 3 or 4;

$R_8$ is hydroxyl, thiol, carboxyl, (C$_1$–$_4$)alkoxycarbonyl, carbamoyl, amino, sulfamoyl, (C$_1$–C$_4$)alkoxy, fluorinated (C$_1$–C$_4$)alkoxy having from 1 to 9 fluorines, (C$_1$–C$_4$)alkylthio, (C$_1$–C$_4$)alkylsulfonyl, (C$_1$–C$_4$) alkylsulfinyl, mono-N- or di-N,N-(C$_1$–C$_4$) alkylcarbamoyl, mono-N- or di-N,N-(C$_1$–C$_4$) alkylamino, (C$_1$–C$_4$)alkylsulfonylamino, fluorinated (C$_1$–C$_4$)alkylsulfonylamino having from 1 to 9 fluorines, (C$_1$–C$_4$)alkanoylamino, fluorinated (C$_1$–C$_4$) alkanoylamino having from 1 to 9 fluorines, mono-N- or di-N,N-(C$_1$–C$_4$)alkylaminosulfonyl, ureido, mono-N- or di-N,N-(C$_1$–C$_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be $(C_1-C_7)$alkyl.

24. A method of treating atherosclerosis which comprises administering to a mammal in need of such treatment an atherosclerosis treating amount of a compound of Formula I or the pharmaceutically acceptable cationic and anionic salts and stereoisomers thereof

FORMULA I

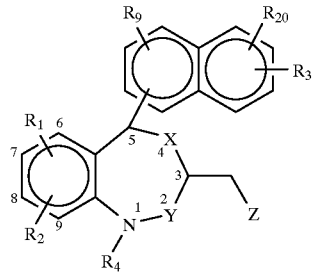

wherein X is oxy, thio, —S(O)— or —S(O)$_2$—;
Y is carbonyl or methylene;
$R_1$, $R_2$, $R_3$, $R_{20}$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl($C_1-C_6$)alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;
$R_4$ is $(C_1-C_7)$alkenyl or $R_4$ is $(C_1-C_7)$alkyl, $(C_1-C_7)$alkenyl or $(C_3-C_4)$cycloalkylmethyl wherein said $(C_1-C_7)$alkyl, $(C_1-C_7)$alkenyl or $(C_3-C_4)$cycloalkylmethyl are mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, mono-N- or di-N,N-$(C_1-C_4)$alkylamino, mono-N- or di-N,N-$(C_1-C_4)$alkylaminocarbonyl, or mono-N- or di-N,N-$(C_1-C_4)$alkylaminosulfonyl; or
$R_4$ is $(C_1-C_7)$alkyl substituted with 1 to 15 fluorines or $(C_3-C_4)$cycloalkylmethyl substituted with 1 to 9 fluorines; or
$R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;
Z is carboxyl, $(C_1-C_4)$alkoxycarbonyl, mono-N- or di-N,N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$($C_1-C_4$)alkyl, N(R$_{12}$)COR$_{15}$,

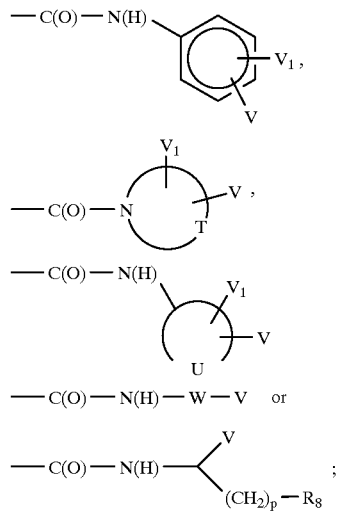

$R_{12}$, $R_{13}$ and $R_{14}$ are each independently H or $(C_1-C_4)$alkyl;
$R_{15}$ is H or $(C_1-C_4)$alkyl;
$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;
T forms a four to seven membered mono-aza, saturated ring, said ring optionally containing thio and said ring optionally mono-substituted on carbon with hydroxyl;
U forms a three to seven membered saturated carbocyclic ring;
V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;
$V_1$ is H, —CO$_2$R$_7$, hydroxyl or $(C_1-C_4)$alkoxy;
$R_7$ is hydrogen or $(C_1-C_4)$alkyl;
p is 1, 2, 3 or 4;
$R_1$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$alkylsulfinyl, mono-N- or di-N,N-$(C_1-C_4)$alkylcarbamoyl, mono-N- or di-N,N-$(C_1-C_4)$alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$alkanoylamino having from 1 to 9 fluorines, mono-N- or di-N,N-($C_1$–$C_4$)alkylaminosulfonyl, ureido, mono-N- or di-N,N-($C_1$–$C_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be ($C_1$–$C_7$)alkyl.

25. A method for the treatment of a fungal infection in a mammal in need of such treatment which comprises administering to the mammal an antifungal treating effective amount of a compound of Formula I or the pharmaceutically acceptable cationic and anionic salts and stereoisomers thereof

FORMULA I

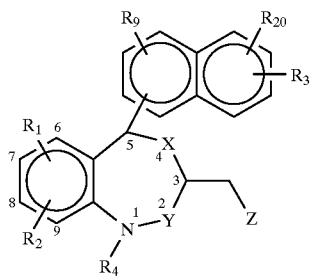

wherein X is oxy, thio, —S(O)— or —S(O)$_2$—;

Y is carbonyl or methylene;

$R_1$, $R_2$, $R_3$, $R_{20}$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfinyl, ($C_1$–$C_4$)alkylsulfonyl, phenyl, amino, mono-N- or di-N,N-($C_1$–$C_4$)alkylamino, carboxyl, ($C_1$–$C_4$)alkoxycarbonyl, carbamoyl, mono-N- or di-N,N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–$C_6$)alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkenyl or $R_4$ is ($C_1$–$C_7$)alkyl, ($C_1$–$C_7$)alkenyl or ($C_3$–$C_4$)cycloalkylmethyl wherein said ($C_1$–$C_7$)alkyl, ($C_1$–$C_7$)alkenyl or ($C_3$–$C_4$)cycloalkylmethyl are mono-, di-, or tri-substituted wherein the substituents are independently chosen from hydroxyl, oxo, ($C_1$–$C_4$)alkyl, amino, carboxy, thiol, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfinyl, ($C_1$–$C_4$)alkylsulfonyl, mono-N- or di-N, N-($C_1$–$C_4$)alkylamino, mono-N- or di-N,N-($C_1$–$C_4$)alkylaminocarbonyl, or mono-N- or di-N,N($C_1$–$C_4$)alkylaminosulfonyl; or $R_4$ is ($C_1$–$C_7$)alkyl substituted with 1 to 15 fluorines or ($C_3$–$C_4$)cycloalkylmethyl substituted with 1 to 9 fluorines; or $R_4$ is het($C_1$–$C_6$)alkyl wherein het is a 4–7 member saturated or unsaturated heterocycle containing independently one to three O, N or S atoms and said het is optionally mono-substituted with ($C_1$–$C_4$)alkyl, ($C_1$–$C_4$)alkoxy, hydroxyl, halo, amino or mono-N- or di-N,N-($C_1$–$C_4$)alkylamino;

Z is carboxyl, ($C_1$–$C_4$)alkoxycarbonyl, mono-N- or di-N, N-($C_1$–$C_4$)alkylaminocarbonyl, aminocarbonyl, cyano, hydroxyaminocarbonyl, —C(O)N(H)SO$_2$R$_1$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N($R_{12}$)CONR$_{13}$R$_{14}$, N($R_{12}$)CO$_2$ ($C_1$–$C_4$)alkyl, N($R_{12}$)COR$_{15}$,

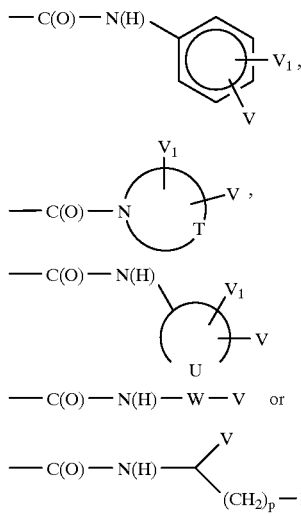

$R_{12}$, $R_{13}$ and $R_{14}$ are each independently H or ($C_1$–$C_4$) alkyl;

$R_{15}$ is H or ($C_1$–$C_4$)alkyl;

$R_5$ is amino or mono-N- or di-N,N-($C_1$–$C_4$)alkylamino; or $R_5$ is ($C_1$–$C_4$)alkyl optionally substituted with 1 to 9 fluorines, amino, mono-N- or di-N,N-($C_1$–$C_4$) alkylamino, carboxyl, ($C_1$–$C_4$)alkoxycarbonyl, carbamoyl or mono-N- or di-N,N-($C_1$–$C_4$) alkylcarbamoyl; phenyl optionally mono- or di-substituted independently with methyl, methoxyl, fluoro, trifluoromethoxyl, carboxyl, ($C_1$–$C_4$) alkoxycarbonyl, methylthio, methylsulfinyl, methylsulfonyl, ($C_1$–$C_4$)alkylsulfonylamino or mono-N- or di-N,N-($C_1$–$C_4$)alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO$_2$R$_7$, hydroxyl or ($C_1$–$C_4$)alkoxy;

$R_7$ is hydrogen or ($C_1$–$C_4$)alkyl;

p is 1, 2, 3 or 4;

$R_8$ is hydroxyl, thiol, carboxyl, ($C_1$–$C_4$)alkoxycarbonyl, carbamoyl, amino, sulfamoyl, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfonyl, ($C_1$–$C_4$)

alkylsulfinyl, mono-N- or di-N,N-$(C_1-C_4)$ alkylcarbamoyl, mono-N- or di-N,N-$(C_1-C_4)$ alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$ alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be $(C_1-C_7)$alkyl.

26. A method for the treatment of acne in a mammal in need of such treatment which comprises administering to the mammal an acne treating amount of a compound of Formula I or the pharmaceutically acceptable cationic and anionic salts and stereoisomers thereof

FORMULA I

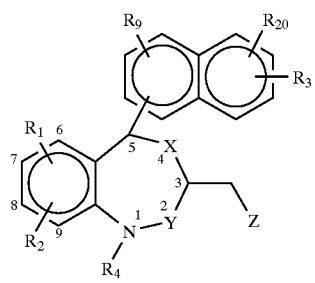

wherein X is oxy, thio, —S(O)— or —S(O)$_2$—;

Y is carbonyl or methylene;

$R_1$, $R_2$, $R_3$, $R_{20}$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N, N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$ alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is $(C_1-C_7)$alkenyl or $R_4$ is $(C_1-C_7)$alkyl, $(C_1-C_7)$ alkenyl or $(C_3-C_4)$cycloalkylmethyl wherein said $(C_1-C_7)$alkyl, $(C_1-C_7)$alkenyl or $(C_3-C_4)$ cycloalkylmethyl are mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$ alkylsulfinyl, $(C_1-C_4)$alkylsulfonyl, mono-N- or di-N, N-$(C_1-C_4)$alkylamino, mono-N- or di-N,N-$(C_1-C_4)$ alkylaminocarbonyl, or mono-N- or di-N,N$(C_1-C_4)$ alkylaminosulfonyl; or $R_4$ is $(C_1-C_7)$alkyl substituted with 1 to 15 fluorines or $(C_3-C_4)$cycloalkylmethyl substituted with 1 to 9 fluorines; or $R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, mono-N- or di-N, N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ $(C_1-C_4)$alkyl, N(R$_{12}$)COR$_{15}$,

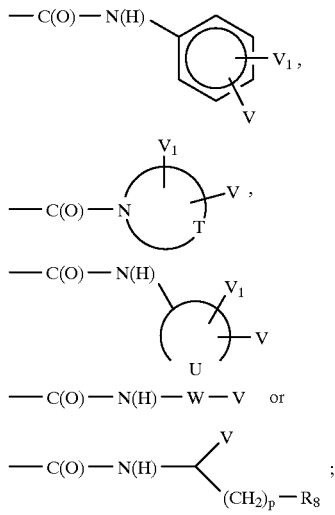

$R_{12}$, $R_{13}$ and $R_{14}$ are each independently H or $(C_1-C_4)$ alkyl;

$R_{15}$ is H or $(C_1-C_4)$alkyl;

$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$ alkylamino, carboxyl, $(C_1-C_4)$alkoxycarbonyl, carbamoyl or mono-N- or di-N,N-$(C_1-C_4)$ alkylcarbamoyl; phenyl optionally mono- or di-substituted independently with methyl, methoxyl, fluoro, trifluoromethoxyl, carboxyl, $(C_1-C_4)$ alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl;

T forms a four to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$V_1$ is H, —CO$_2$R$_7$, hydroxyl or $(C_1-C_4)$alkoxy;

$R_7$ is hydrogen or $(C_1-C_4)$alkyl;

p is 1, 2, 3 or 4;

$R_8$ is hydroxyl, thiol, carboxyl, $(C_1-C_4)$alkoxycarbonyl, carbamoyl, amino, sulfamoyl, $(C_1-C_4)$alkoxy, fluorinated ($C_1$–$C_4$)alkoxy having from 1 to 9 fluorines, ($C_1$–$C_4$)alkylthio, ($C_1C_1$–$C_4$)alkylsulfonyl, ($C_1$–$C_4$)alkylsulfinyl, mono-N- or di-N,N-($C_1$–$C_4$)alkylcarbamoyl, mono-N- or di-N,N-($C_1$–$C_4$)alkylamino, ($C_1$–$C_4$)alkylsulfonylamino, fluorinated ($C_1$–$C_4$)alkylsulfonylamino having from 1 to 9 fluorines, ($C_1$–$C_4$)alkanoylamino, fluorinated ($C_1$–$C_4$)alkanoylamino having from 1 to 9 fluorines, mono-N- or di-N,N-($C_1$–$C_4$)alkylaminosulfonyl, ureido, mono-N- or di-N,N-($C_1$–$C_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl with the proviso that $R_4$ cannot be ($C_1$–$C_7$)alkyl.

* * * * *